US006228589B1

(12) United States Patent
Brenner

(10) Patent No.: US 6,228,589 B1
(45) Date of Patent: May 8, 2001

(54) MEASUREMENT OF GENE EXPRESSION PROFILES IN TOXICITY DETERMINATION

(75) Inventor: Sydney Brenner, Cambridge (GB)

(73) Assignee: Lynx Therapeutics, Inc., Hayward, CA (US)

( * ) Notice: Subject to any disclaimer, the term of this patent is extended or adjusted under 35 U.S.C. 154(b) by 0 days.

(21) Appl. No.: 09/269,911

(22) PCT Filed: Oct. 11, 1996

(86) PCT No.: PCT/US96/16342

§ 371 Date: Feb. 28, 2000

§ 102(e) Date: Feb. 28, 2000

(87) PCT Pub. No.: WO97/13877

PCT Pub. Date: Apr. 17, 1997

(51) Int. Cl.[7] ............................. C12Q 1/68; C07H 21/00
(52) U.S. Cl. .................... 435/6; 536/23.1; 536/25.32; 536/25.4; 536/25.6
(58) Field of Search ................... 435/6, 440, 471; 536/23.1, 24.2, 24.3, 25.4, 25.32, 25.6

(56) References Cited

FOREIGN PATENT DOCUMENTS

WO 95/21944    8/1995  (WO) .
WO 97/13877  * 4/1997  (WO) .

OTHER PUBLICATIONS

Brenner, S, and Lerner. R.A., "Encoded combinatorial chemistry." Proc. Natl. Acad. Sci. USA 89:5381–5383 (1992).

Chetverin, A.B., and Kramer, F.R., "Oligonucleotide Arrays: New Concepts and Possibilities." Bio/Technology 12:1093–1099 (1994).

Matsubara, K. and Okubo, K., "cDNA analysis in the human genome project." Gene 135:265–274 (1993).

* cited by examiner

*Primary Examiner*—John L. LeGuyader
*Assistant Examiner*—Mark L. Shibuya
(74) *Attorney, Agent, or Firm*—Stephen C. Macevicz; Vincent M. Powers; LeeAnn Gorthey

(57) ABSTRACT

A method is provided for assessing the toxicity of a compound in a test organism by measuring gene expression profiles of selected tissues. Gene expression profiles are measured by massively parallel signature sequencing of cDNA libraries constructed from mRNA extracted from the selected tissues. Gene expression profiles provide extensive information on the effects of administering a compound to a test organism in both acute toxicity tests and in prolonged and chronic toxicity tests.

20 Claims, 2 Drawing Sheets

SEQUENCE LISTING

<160> NUMBER OF SEQ ID NOS: 10

<210> SEQ ID NO: 1
<211> LENGTH: 11
<212> TYPE: DNA
<213> ORGANISM: Artificial Sequence
<220> FEATURE:
<223> OTHER INFORMATION: conjugate

<400> SEQUENCE: 1
ctagtcgacc a                                                      11

<210> SEQ ID NO: 2
<211> LENGTH: 11
<212> TYPE: DNA
<213> ORGANISM: Artificial Sequence
<220> FEATURE:
<223> OTHER INFORMATION: conjugate
<221> NAME/KEY: misc_feature
<222> LOCATION: (1)...(11)
<223> OTHER INFORMATION: n = A,T,C or G

<400> SEQUENCE: 2
nrrgatcynn n                                                      11

```
<210> SEQ ID NO: 3
<211> LENGTH: 38
<212> TYPE: DNA
<213> ORGANISM: Artificial Sequence
<220> FEATURE:
<223> OTHER INFORMATION: conjugate

<400> SEQUENCE: 3
gaggatgcct ttatggatcc actcgagatc ccaatcca                    38

<210> SEQ ID NO: 4
<211> LENGTH: 20
<212> TYPE: DNA
<213> ORGANISM: Artificial Sequence
<220> FEATURE:
<223> OTHER INFORMATION: conjugate

<400> SEQUENCE: 4
agtggctggg catcggaccg                                        20

<210> SEQ ID NO: 5
<211> LENGTH: 20
<212> TYPE: DNA
<213> ORGANISM: Artificial Sequence
<220> FEATURE:
<223> OTHER INFORMATION: conjugate

<400> SEQUENCE: 5
ggggcccagt cagcgtcgat                                        20

<210> SEQ ID NO: 6
<211> LENGTH: 20
<212> TYPE: DNA
<213> ORGANISM: Artificial Sequence
<220> FEATURE:
<223> OTHER INFORMATION: conjugate

<400> SEQUENCE: 6
atcgacgctg actgggcccc                                        20

<210> SEQ ID NO: 7
<211> LENGTH: 69
<212> TYPE: DNA
<213> ORGANISM: Artificial Sequence
<220> FEATURE:
<223> OTHER INFORMATION: conjugate
<221> NAME/KEY: misc_feature
<222> LOCATION: (65)...(65)
<223> OTHER INFORMATION: n = cDNA from library
<221> NAME/KEY: misc_feature
<222> LOCATION: (66)...(69)
<223> OTHER INFORMATION: n = A,T,C or G

<400> SEQUENCE: 7
rcgaccacww wcwwwcwwwc wwwcwwwcww wcwwwcwwwc wwwggttttt       60 ttttnnnnr                                                    69

<210> SEQ ID NO: 8
<211> LENGTH: 69
<212> TYPE: DNA
<213> ORGANISM: Artificial Sequence
<220> FEATURE:
<223> OTHER INFORMATION: conjugate
<221> NAME/KEY: misc_feature
<222> LOCATION: (61)...(61)
<223> OTHER INFORMATION: n = rDNA complement
```

-continued

```
<221> NAME/KEY: misc_feature
<222> LOCATION: (62)...(69)
<223> OTHER INFORMATION: n = A,T,C or G
<221> NAME/KEY: misc_feature
<222> LOCATION: (1)...(69)
<223> OTHER INFORMATION: complement to SEQ ID NO: 7

<400> SEQUENCE: 8
ggtgwwwgww wgwwwgwwwg wwwgwwwgww wgwwwgwwwc caaaaaaaaa aaaaaaaaa        60 nnnnyctag                                                               69

<210> SEQ ID NO: 9
<211> LENGTH: 24
<212> TYPE: DNA
<213> ORGANISM: Artificial Sequence
<220> FEATURE:
<223> OTHER INFORMATION: conjugate
<221> NAME/KEY: misc_feature
<222> LOCATION: (1)...(24)
<223> OTHER INFORMATION: n = A,T,C or G

<400> SEQUENCE: 9
tagynnnnnn nnnnnnnnnn nnnn                                              24

<210> SEQ ID NO: 10
<211> LENGTH: 24
<212> TYPE: DNA
<213> ORGANISM: Artificial Sequence
<220> FEATURE:
<223> OTHER INFORMATION: conjugate
<221> NAME/KEY: misc_feature
<222> LOCATION: (1)...(24)
<223> OTHER INFORMATION: n = A,T,C or G

<400> SEQUENCE: 10
gatcnnacta gtnnnnnnnn nnnn                                              24
```

MEASUREMENT OF GENE EXPRESSION PROFILES IN TOXICITY DETERMINATION

FIELD OF THE INVENTION

The invention relates generally to methods for detecting and monitoring phenotypic changes in in vitro and in vivo systems for assessing and/or determining the toxicity of chemical compounds, and more particularly, the invention relates to a method for detecting and monitoring changes in gene expression patterns in in vitro and in vivo systems for determining the toxicity of drug candidates.

BACKGROUND

The ability to rapidly and conveniently assess the toxicity of new compounds is extremely important. Thousands of new compounds are synthesized every year, and many are introduced to the environment through the development of new commercial products and processes, often with little knowledge of their short term and long term health effects. In the development of new drugs, the cost of assessing the safety and efficacy of candidate compounds is becoming astronomical. It is estimated that the pharmaceutical industry spends an average of about 300 million dollars to bring a new pharmaceutical compound to market, e.g. Biotechnology. 13: 226–228 (1995). A large fraction of these costs are due to the failure of candidate compounds in the later stages of the developmental process. That is, as the assessment of a candidate drug progresses from the identification of a compound as a drug candidate—for example, through relatively inexpensive binding assays or in vitro screening assays, to pharmacokinetic studies, to toxicity studies, to efficacy studies in model systems. to preliminary clinical studies, and so on, the costs of the associated tests and analyses increases tremendously. Consequently, it may cost several tens of millions of dollars to determine that a once promising candidate compound possesses a side effect or cross reactivity that renders it commercially infeasible to develop further. A great challenge of pharmaceutical development is to remove from further consideration as early as possible those compounds that are likely to fail in the later stages of drug testing.

Drug development programs are clearly structured with this objective in mind, however, rapidly escalating costs have created a need to develop even more stringent and less expensive screens in the early stages to identify false leads as soon as possible. Toxicity assessment is an area where such improvements may be made. for both drug development and for assessing the environmental, health, and safety effects of new compounds in general.

Typically the toxicity of a compound is determined by administering the compound to one or more species of test animal under controlled conditions and by monitoring the effects on a wide range of parameters. The parameters include such things as blood chemistry, weight gain or loss, a variety of behavioral patterns, muscle tone, body temperature, respiration rate, lethality, and the like, which collectively provide a measure of the state of health of the test animal. The degree of deviation of such parameters from their normal ranges gives a measure of the toxicity of a compound. Such tests may be designed to assess the acute, prolonged, or chronic toxicity of a compound. In general, acute tests involve administration of the test chemical on one occasion. The period of observation of the test animals may be as short as a few hours, although it is usually at least 24 hours and in some cases it may be as long as a week or more. In general, prolonged tests involve administration of the test chemical on multiple occasions. The test chemical may be administered one or more times each day, irregularly as when it is incorporated in the diet, at specific times such as during pregnancy, or in some cases regularly but only at weekly intervals. Also, in the prolonged test the experiment is usually conducted for not less than 90 days in the rat or mouse or a year in the dog. In contrast to the acute and prolonged types of test, the chronic toxicity tests are those in which the test chemical is administered for a substantial portion of the lifetime of the test animal. In the case of the mouse or rat, this is a period of 2 to 3 years. In the case of the dog, it is for 5 to 7 years.

Significant costs are incurred in establishing and maintaining large cohorts of test animals for such assays, especially the larger animals in chronic toxicity assays. Moreover, because of species specific effects, passing such toxicity tests does not ensure that a compound is free of toxic effects when used in humans. Such tests do, however, provide a standardized set of information for judging the safety of new compounds, and they provide a database for giving preliminary assessments of related compounds. An important area for improving toxicity determination would be the identification of new observables which are predictive of the outcome of the expensive and tedious animal assays.

In other medical fields, there has been significant interest in applying recent advances in biotechnology, particularly in DNA sequencing, to the identification and study of differentially expressed genes in healthy and diseased organisms, e.g. Adams et al, Science, 252: 1651–1656 (1991); Matsubara et al, Gene, 135: 265–274 (1993); Rosenberg et al, International patent application, PCT/US95/01863. The objectives of such applications include increasing our knowledge of disease processes, identifying genes that play important roles in the disease process, and providing diagnostic and therapeutic approaches that exploit the expressed genes or their products. While such approaches are attractive, those based on exhaustive, or even sampled, sequencing of expressed genes are still beset by the enormous effort required: It is estimated that 30–35 thousand different genes are expressed in a typical mammalian tissue in any given state, e.g. Ausubel et al, Editors, Current Protocols, 5.8.1–5.8.4 (John Wiley & Sons, New York, 1992). Determining the sequences of even a small sample of that number of gene products is a major enterprise, requiring industrial-scale resources. Thus, the routine application of massive sequencing of expressed genes is still beyond current commercial technology.

The availability of new assays for assessing the toxicity of compounds, such as candidate drugs, that would provide more comprehensive and precise information about the state of health of a test animal would be highly desirable. Such additional assays would preferably be less expensive, more rapid, and more convenient than current testing procedures, and would at the same time provide enough information to make early judgments regarding the safety of new compounds.

SUMMARY OF THE INVENTION

An object of the invention is to provide a new approach to toxicity assessment based on an examination of gene expression patterns, or profiles, in in vitro or in vivo test systems.

Another object of the invention is to provide a database on which to base decisions concerning the toxicological properties of chemicals, particularly drug candidates.

A further object of the invention is to provide a method for analyzing gene expression patterns in selected tissues of test animals.

A still further object of the invention is to provide a system for identifying genes which are differentially expressed in response to exposure to a test compound.

Another object of the invention is to provide a rapid and reliable method for correlating gene expression with short term and long term toxicity in test animals.

Another object of the invention is to identify genes whose expression is predictive of deleterious toxicity.

The invention achieves these and other objects by providing a method for massively parallel signature sequencing of genes expressed in one or more selected tissues of an organism exposed to a test compound. An important feature of the invention is the application of novel DNA sorting and sequencing methodologies that permit the formation of gene expression profiles for selected tissues by determining the sequence of portions of many thousands of different polynucleotides in parallel. Such profiles may be compared with those from tissues of control organisms at single or multiple time points to identify expression patterns predictive of toxicity.

The sorting methodology of the invention makes use of oligonucleotide tags that are members of a minimally cross-hybridizing set of oligonucleotides. The sequences of oligonucleotides of such a set differ from the sequences of every other member of the same set by at least two nucleotides. Thus, each member of such a set cannot form a duplex (or triplex) with the complement of any other member with less than two mismatches. Complements of oligonucleotide tags of the invention, referred to herein as "tag complements," may comprise natural nucleotides or non-natural nucleotide analogs. Preferably, tag complements are attached to solid phase supports. Such oligonucleotide tags when used with their corresponding tag complements provide a means of enhancing specificity of hybridization for sorting polynucleotides, such as cDNAs.

The polynucleotides to be sorted each have an oligonucleotide tag attached, such that different polynucleotides have different tags. As explained more fully below, this condition is achieved by employing a repertoire of tags substantially greater than the population of polynucleotides and by taking a sufficiently small sample of tagged polynucleotides from the full ensemble of tagged polynucleotide. After such sampling, when the populations of supports and polynucleotides are mixed under conditions which permit specific hybridization of the oligonucleotide tags with their respective complements, identical polynucleotides sort onto particular beads or regions. The sorted populations of polynucleotides can then be sequenced on the solid phase support by a "single-base" or "base-by-base" sequencing methodology, as described more fully below.

In one aspect, the method of the invention comprises the following steps: (a) administering the compound to a test organism; (b) extracting a population of mRNA molecules from each of one or more tissues of the test organism; (c) forming a separate population of cDNA molecules from each population of mRNA molecules extracted from the one or more tissues such that each cDNA molecule of the separate populations has an oligonucleotide tag attached, the oligonucleotide tags being selected from the same minimally cross-hybridizing set; (d) separately sampling each population of cDNA molecules such that substantially all different cDNA molecules within a separate population have different oligonucleotide tags attached; (e) sorting the cDNA molecules of each separate population by specifically hybridizing the oligonucleotide tags with their respective complements, the respective complements being attached as uniform populations of substantially identical complements in spatially discrete regions on one or more solid phase supports; (f) determining the nucleotide sequence of a portion of each of the sorted cDNA molecules of each separate population to form a frequency distribution of expressed genes for each of the one or more tissues; and (g) correlating the frequency distribution of expressed genes in each of the one or more tissues with the toxicity of the compound.

An important aspect of the invention is the identification of genes whose expression is predictive of the toxicity of a compound. Once such genes are identified, they may be employed in conventional assays, such as reverse transcriptase polymerase chain reaction (RT-PCR) assays for gene expression.

DEFINITIONS

Figure 1:
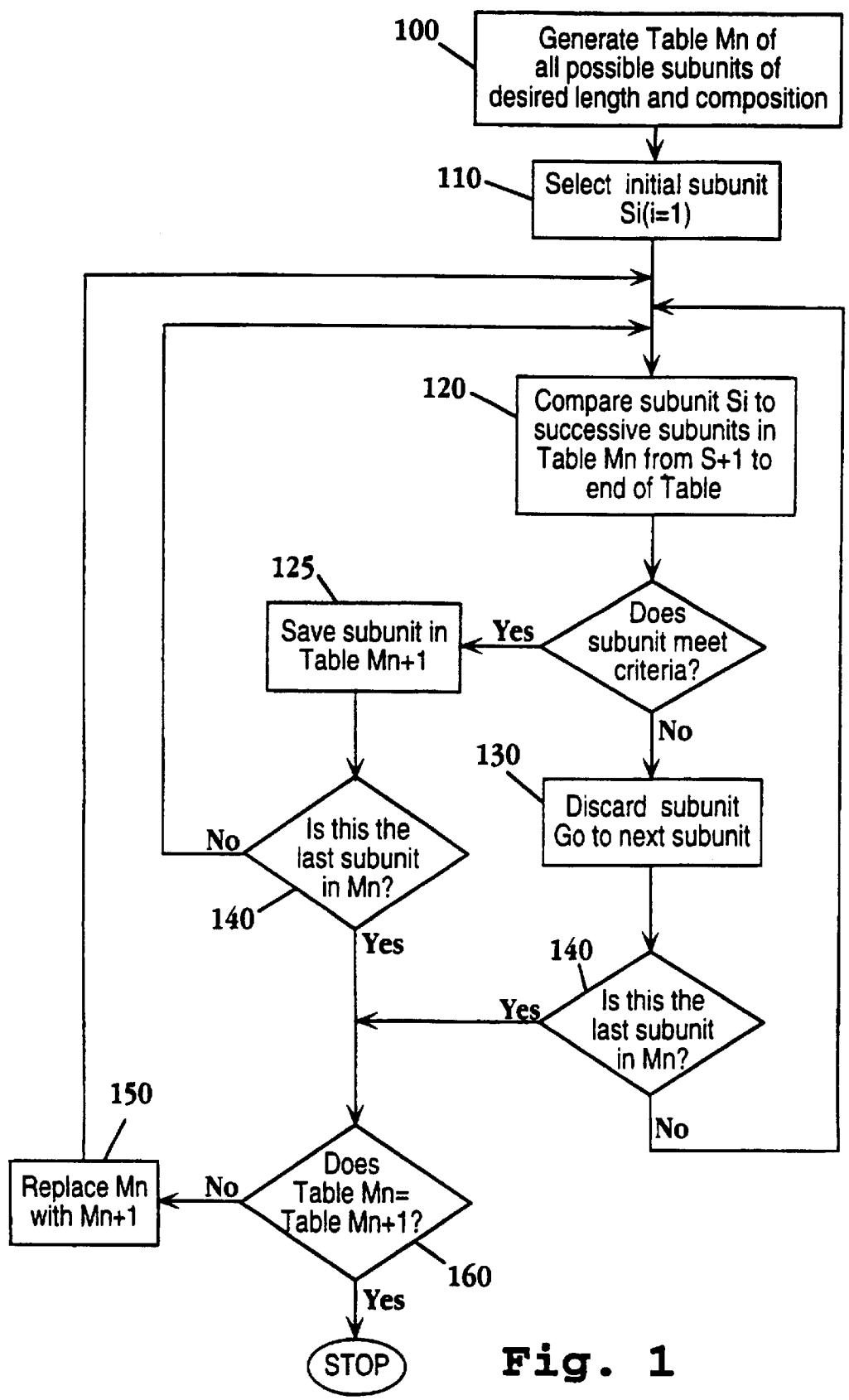
FIG. 1 is a flow chart representation of an algorithm for generating minimally cross-hybridizing sets of oligonucleotides.

"Complement" or "tag complement" as used herein in reference to oligonucleotide tags refers to an oligonucleotide to which a oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

The term "oligonucleotide" as used herein includes linear oligomers of natural or modified monomers or linkages, including deoxyribonucleosides, ribonucleosides, anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several tens of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphormidate, and the like. Usually oligonucleotides of the invention comprise the four natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

As used herein, "nucleoside" includes the natural nucleosides, including 2'-deoxy and 2'-hydroxyl forms, e.g. as described in Komberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleosides designed to enhance binding properties, reduce complexity, increase specificity, and the like.

As used herein "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identification, ordering, and locations of one, two, or three of the four types of nucleotides within a target polynucleotide. For example, in some embodiments sequence determination may be effected by identifying the ordering and locations of a single type of nucleotide, e.g. cytosines, within the target polynucleotide "CATCGC . . . " so that its sequence is represented as a binary code, e.g. "100101 . . . " for "C-(not C)-(not C)-C-(not C-C . . . " and the like.

As used herein, the term "complexity" in reference to a population of polynucleotides means-the number of different species of molecule present in the population.

As used herein, the terms "gene expression profile," and "gene expression pattern" which is used equivalently, means a frequency distribution of sequences of portions of cDNA molecules sampled from a population of tag-cDNA conjugates. Generally, the portions of sequence are sufficiently long to uniquely identify the cDNA from which the portion arose. Preferably, the total number of sequences determined is at least 1000; more preferably, the total number of sequences determined in a gene expression profile is at least ten thousand.

As used herein, "test organism" means any in vitro or in vivo system which provides measureable responses to exposure to test compounds. Typically, test organisms may be mammalian cell cultures, particularly of specific tissues, such as hepatocytes, neurons, kidney cells, colony forming cells, or the like, or test organisms may be whole animals, such as rats, mice, hamsters, guinea pigs, dogs, cats, rabbits, pigs, monkeys, and the like.

DETAILED DESCRIPTION OF THE INVENTION

The invention provides a method for determining the toxicity of a compound by analyzing changes in the gene expression profiles in selected tissues of test organisms exposed to the compound. The invention also provides a method of identifying toxicity markers consisting of individual genes or a group of genes that is expressed acutely and which is correlated with prolonged or chronic toxicity, or suggests that the compound will have an undesirable cross reactivity. Gene expression profiles are generated by sequencing portions of cDNA molecules construction from mRNA extracted from tissues of test organisms exposed to the compound being tested. As used herein, the term "tissue" is employed with its usual medical or biological meaning, except that in reference to an in vitro test system, such as a cell culture, it simply means a sample from the culture. Gene expression profiles derived from test organisms are compared to gene expression profiles derived from control organisms to determine the genes which are differentially expressed in the test organism because of exposure to the compound being tested. In both cases, the sequence information of the gene expression profiles is obtained by massively parallel signature sequencing of cDNAs, which is implemented in steps (c) through (f) of the above method.

Toxicity Assessment

Procedures for designing and conducting toxicity tests in in vitro and in vivo systems is well known, and is described in many texts on the subject, such as Loomis et al. Loomis's Esstentials of Toxicology, 4th Ed. (Academic Press, New York, 1996); Echobichon, The Basics of Toxicity Testing (CRC Press, Boca Raton, 1992); Frazier, editor, In Vitro Toxicity Testing (Marcel Dekker, New York, 1992); and the like.

In toxicity testing, two groups of test organisms are usually employed: one group serves as a control and the other group receives the test compound in a single dose (for acute toxicity tests) or a regimen of doses (for prolonged or chronic toxicity tests). Since in most cases, the extraction of tissue as called for in the method of the invention requires sacrificing the test animal, both the control group and the group receiving compound must be large enough to permit removal of animals for sampling tissues, if it is desired to observe the dynamics of gene expression through the duration of an experiment.

In setting up a toxicity study, extensive guidance is provided in the literature for selecting the appropriate test organism for the compound being tested, route of administration. dose ranges, and the like. Water or physiological saline (0.9% NaCl in water) is the solute of choice for the test compound since these solvents permit administration by a variety of routes. When this is not possible because of solubility limitations, it is necessary to resort to the use of vegetable oils such as corn oil or even organic solvents, of which propylene glycol is commonly used. Whenever possible the use of suspension of emulsion should be avoided except for oral administration. Regardless of the route of administration, the volume required to administer a given dose is limited by the size of the animal that is used. It is desirable to keep the volume of each dose uniform within and between groups of animals. When rates or mice are used the volume administered by the oral route should not exceed 0.005 ml per gram of animal. Even when aqueous or physiological saline solutions are used for parenteral injection the volumes that are tolerated are limited, although such solutions are ordinarily thought of as being innocuous. The intravenous $LD_{50}$ of distilled water in the mouse is approximately 0.044 ml per gram and that of isotonic saline is 0.068 ml per gram of mouse.

When a compound is to be administered by inhalation, special techniques for generating test atmospheres are necessary. Dose estimation becomes very complicated. The methods usually involve aerosolization or nebulization of fluids containing the compound. If the agent to be tested is a fluid that has an appreciable vapor pressure, it may be administered by passing air through the solution under controlled temperature conditions. Under these conditions, dose is estimated from the volume of air inhaled per unit time, the temperature of the solution, and the vapor pressure of the agent involved. Gases are metered from reservoirs. When particles of a solution are to be administered, unless the particle size is less than about 2 $\mu$m the particles will not reach the terminal alveolar sacs in the lungs. A variety of apparatuses and chambers are available to perform studies for detecting effects of irritant or other toxic endpoints when they are administered by inhalation. The preferred method of administering an agent to animals is via the oral route, either by intubation or by incorporating the agent in the feed.

Preferably, in designing a toxicity assessment, two or more species should be employed that handle the test compound as similarly to man as possible in terms of metabolism, absorption, excretion, tissue storage, and the like. Preferably, multiple doses or regimens at different concentrations should be employed to establish a dose-response relationship with respect to toxic effects. And preferably, the route of administration to the test animal should be the same as, or as similar as possible to, the route of administration of the compound to man. Effects obtained by one route of administration to test animals are not a priori applicable to effects by another route of administration to man. For example, food additives for man should be tested by admixture of the material in the diet of the test animals.

Acute toxicity tests consist of administering a compound to test organisms on one occasion. The purpose of such test is to determine the symptomotology consequent to administration of the compound and to determine the degree of lethality of the compound. The initial procedure is to perform a series of range-finding doses of the compound in a single species. This necessitates selection of a route of administration, preparation of the compound in a form suitable for administration by the selected route, and selection of an appropriate species. Preferably, initial acute toxicity studies are performed on either rats or mice because of their low cost, their availability, and the availability of abundant toxicologic reference data on these species. Prolonged toxicity tests consist of administering a compound to test organisms repeatedly, usually on a daily basis, over a period of 3 to 4 months. Two practical factors are encountered that place constraints on the design of such tests: First, the available routes of administration are limited because the route selected must be suitable for repeated administration without inducing harmful effects. And second, blood,. urine, and perhaps other samples, should be taken repeatedly without inducing significant harm to the test animals. Preferably, in the method of the invention the gene expression profiles are obtained in conjunction with the measurement of the traditional toxicologic parameters, such as listed in the table below:

| Hematology | Blood Chemistry | Urine Analyses |
| --- | --- | --- |
| erythrocyte count | sodium | pH |
| total leukocyte count | potassium | specific gravity |
| differential leukocyte count | chloride | total protein |
| hematocrit | calcium | sediment |

-continued

| Hematology | Blood Chemistry | Urine Analyses |
| --- | --- | --- |
| hemoglobin | carbon dioxide | glucose |
|  | serum glutamine-pyruvate transaminase | ketones |
|  | serum glutamin-oxalacetic transaminase | bilirubin |
|  | serum protein electrophoresis |  |
|  | blood sugar |  |
|  | blood urea nitrogen |  |
|  | total serum protein |  |
|  | serum albumin |  |
|  | total serum bilirubin |  |

Oligonucleotide Tags and Tag Complements

Oligonucleotide tags are members of a minimally cross-hybridizing set of oligonucleotides. The sequences of oligonucleotides of such a set differ from the sequences of every other member of the same set by at least two nucleotides. Thus, each member of such a set cannot form a duplex (or triplex) with the complement of any other member with less than two mismatches. Complements of oligonucleotide tags, referred to herein as "tag complements," may comprise natural nucleotides or non-natural nucleotide analogs. Preferably, tag complements are attached to solid phase supports. Such oligonucleotide tags when used with their corresponding tag complements provide a means of enhancing specificity of hybridization for sorting, tracking, or labeling molecules, especially polynucleotides.

Minimally cross-hybridizing sets of oligonucleotide tags and tag complements may be synthesized either combinatorially or individually depending on the size of the set desired and the degree to which cross-hybridization is sought to be minimized (or stated another way, the degree to which specificity is sought to be enhanced). For example, a minimally cross-hybridizing set may consist of a set of individually synthesized 10-mer sequences that differ from each other by at least 4 nucleotides. such set having a maximum size of 332 (when composed of 3 kinds of nucleotides and counted using a computer program such as disclosed in Appendix Ic). Alternatively, a minimally cross-hybridizing set of oligonucleotide tags may also be assembled combinatorially from subunits which themselves are selected from a minimally cross-hybridizing set. For example, a set of minimally cross-hybridizing 12-mers differing from one another by at least three nucleotides may be synthesized by assembling 3 subunits selected from a set of minimally cross-hybridizing 4-mers that each differ from one another by three nucleotides. Such an embodiment gives a maximally sized set of $9^3$, or 729, 12-mers. The number 9 is number of oligonucleotides listed by the computer program of Appendix Ia, which assumes, as with the 10-mers, that only 3 of the 4 different types of nucleotides are used. The set is described as "maximal" because the computer programs of Appendices Ia–c provide the largest set for a given input (e.g. length, composition, difference in number of nucleotides between members). Additional minimally cross-hybridizing sets may be formed from subsets of such calculated sets.

Oligonucleotide tags may be single stranded and be designed for specific hybridization to single stranded tag complements by duplex formation or for specific hybridization to double stranded tag complements by triplex formation. Oligonucleotide tags may also be double stranded and be designed for specific hybridization to single stranded tag complements by triplex formation.

When synthesized combinatorially, an oligonucleotide tag preferably consists of a plurality of subunits, each subunit consisting of an oligonucleotide of 3 to 9 nucleotides in length wherein each subunit is selected from the same minimally cross-hybridizing set. In such embodiments, the number of oligonucleotide tags available depends on the number of subunits per tag and on the length of the subunits. The number is generally much less tana the number of all possible sequences the length of the tag, which for a tag n nucleotides long would be $4^n$.

Complements of oligonucleotide tags attached to a solid phase support are used to sort polynucleotides from a mixture of polynucleotides each containing a tag. Complements of the oligonucleotide tags are synthesized on the surface of a solid phase support, such as a microscopic bead or a specific location on an array of synthesis locations on a single support, such that populations of identical sequences are produced in specific regions. That is, the surface of each support, in the case of a bead, or of each region, in the case of an array, is derivatized by only one type of complement which has a particular sequence. The population of such beads or regions contains a repertoire of complements with distinct sequences. As used herein in reference to oligonucleotide tags and tag complements, the term "repertoire" means the set of minimally cross-hybridizing set of oligonucleotides that make up the tags in a particular embodiment or the corresponding set of tag complements.

The polynucleotides to be sorted each have an oligonucleotide tag attached, such that different polynucleotides have different tags. As explained more fully below, this condition is achieved by employing a repertoire of tags substantially greater than the population of polynucleotides and by taking a sufficiently small sample of tagged polynucleotides from the full ensemble of tagged polynucleotides. After such sampling, when the populations of supports and polynucleotides are mixed under conditions which permit specific hybridization of the oligonucleotide tags with their respective complements, identical polynucleotides sort onto particular beads or regions.

The nucleotide sequences of oligonucleotides of a minimally cross-hybridizing set are conveniently enumerated by simple computer programs, such as those exemplified by programs whose source codes are listed in Appendices Ia and Ib. Program minhx of Appendix Ia computes all minimally cross-hybridizing sets having 4mer -subunits composed of three kinds of nucleotides. Program tagN of Appendix Ib enumerates longer oligonucleotides of a minimally cross-hybridizing set. Similar algorithms and computer programs are readily written for listing oligonucleotides of minimally cross-hybridizing sets for any embodiment of the invention. Table I below provides guidance as to the size of sets of minimally cross-hybridizing oligonucleotides for the indicated lengths and number of nucleotide differences. The above computer programs were used to generate the numbers.

TABLE I

| Oligonucleotide Word Length | Nucleotide Difference between Oligonucleolides of Minimally Cross-Hybridizing Set | Maximal Size of Minimally Cross-Hybridizing Set | Size of Repertoire with Four Words | Size of Repertoire with Five Words |
|---|---|---|---|---|
| 4 | 3 | 9 | 6561 | $5.90 \times 10^4$ |
| 6 | 3 | 27 | $5.3 \times 10^5$ | $1.43 \times 10^7$ |
| 7 | 4 | 27 | $5.3 \times 10^5$ | $1.43 \times 10^7$ |
| 7 | 5 | 8 | 4096 | $3.28 \times 10^4$ |
| 8 | 3 | 190 | $1.30 \times 10^9$ | $2.48 \times 10^{11}$ |
| 8 | 4 | 62 | $1.48 \times 10^7$ | $9.16 \times 10^8$ |
| 8 | 5 | 18 | $1.05 \times 10^5$ | $1.89 \times 10^6$ |
| 9 | 5 | 39 | $2.31 \times 10^6$ | $9.02 \times 10^7$ |
| 10 | 5 | 332 | $1.21 \times 10^{10}$ | |
| 10 | 6 | 28 | $6.15 \times 10^5$ | $1.72 \times 10^7$ |
| 11 | 5 | 187 | | |
| 18 | 6 | ≈25000 | | |
| 18 | 12 | 24 | | |

For some embodiments of the invention, where extremely large repertoires of tags are not required, oligonucleotide tags of a minimally cross-hybridizing set may be separately synthesized. Sets containing several hundred to several thousands, or even several tens of thousands, of oligonucleotides may be synthesized directly by a variety of parallel synthesis approaches, e.g. as disclosed in Frank et al, U.S. Pat. No. 4,689,405; Frank et al, Nucleic Acids Research, 11: 4365–4377 (1983); Matson et al, Anal. Biochem., 224: 110–116 (1995); Fodor et al, International application PCT/US93/04145; Pease et al, Proc. Natl. Acad. Sci., 91: 5022–5026 (1994); Southern et al, J. Biotechnology, 35: 217–227 (1994), Brennan, International application PCT/US94/05896; Lashkari et al, Proc. Natl. Acad. Sci., 92: 7912–7915 (1995); or the like.

Preferably, oligonucleotide tags of the invention are synthesized combinatorially out of subunits between three and six nucleotides in length and selected from the same minimally cross-hybridizing set. For oligonucletides in this range, the members of such sets may be enumerated by computer programs based on the algorithm of FIG. 1.

The algorithm of FIG. 1 is implemented by first defming the characteristics of the subunits of the minimally cross-hybridizing set, i.e. length, number of base differences between members, and composition, e.g. do they consist of two, three, or four kinds of bases. A table $M_n$, n=1, is generated (100) that consists of all possible sequences of a given length and composition. An initial subunit $S_1$ is selected and compared (120) with successive subunits $S_i$ for i=n+1 to the end of the table. Whenever a successive subunit has the required number of mismatches to be a member of the minimally cross-hybridizing set, it is saved in a new table $M_{n+1}$ (125). that also contains subunits previously selected in prior passes through step 120. For example, in the first set of comparisons, $M_2$ will contain $S_1$; in the second set of comparisons, $M_3$ will contain $S_1$ and $S_2$; in the third set of comparisons, $M_4$ will contain $S_1$, $S_2$, and $S_3$; and so on. Similarly, comparisons in table $M_j$ will be between $S_j$ and all successive subunits in $M_j$. Note that each successive table $M_{n+1}$ is smaller than its predecessors as subunits are eliminated in successive passes through step 130. After every subunit of table $M_n$ has been compared (140) the old table is replaced by the new table $M_{n+1}$, and the next round of comparisons are begun. The process stops (160) when a table $M_n$ is reached that contains no successive subunits to compare to the selected subunit $S_i$, i.e. $M_n=M_{n+1}$.

Preferably, minimally cross-hybridizing sets comprise subunits that make approximately equivalent contributions to duplex stability as every other subunit in the set. In this way, the stability of perfectly matched duplexes between every subunit and its complement is approximately equal. Guidance for selecting such sets is provided by published techniques for selecting optimal PCR primers and calculating duplex stabilities, e.g. Rychlik et al, Nucleic Acids Research, 17: 8543–8551 (1989) and 18: 6409–6412 (1990); Breslauer et al, Proc. Natl. Acad. Sci., 83:3746–3750 (1986); Wetmur, Crit. Rev. Biochem. Mol. Biol., 26: 227–259 (1991);and the like. For shorter tags, e.g. about 30 nucleotides or less, the algorithm described by Rychlik and Wetmur is preferred, and for longer tags, e.g. about 30–35 nucleotides or greater, an algorithm disclosed by Suggs et al, pages 683–693 in Brown, editor, ICN-UCLA Symp. Dev. Biol., Vol. 23 (Academic Press, New York, 1981) may be conveniently employed. Clearly, the are many approaches available to one skilled in the art for designing sets of minimally cross-hybridizing subunits within the scope of the invention. For example, to minimize the affects of different base-stacking energies of terminal nucleotides when subunits are assembled, subunits may be provided that have the same terminal nucleotides. In this way, when subunits are linked, the sum of the base-stacking energies of all the adjoining terminal nucleotides will be the same, thereby reducing or eliminating variability in tag melting temperatures.

A "word" of terminal nucleotides, shown in italic below, may also be added to each end of a tag so that a perfect match is always formed between it and a similar terminal "word" on any other tag complement. Such an augmented tag would have the form:

| W | $W_1$ | $W_2 ... W_{k-1}$ | $W_k$ | W |
|---|---|---|---|---|
| W' | $W_1'$ | $W_2' ... W_{k-1}'$ | $W_k'$ | W' | where the primed W's indicate complements. With ends of tags always forming perfectly matched duplexes, all mismatched words will be internal mismatches thereby reducing the stability of tag-complement duplexes that otherwise would have mismatched words at their ends. It is well known that duplexes with internal mismatches are significantly less stable tand duplexes with the same mismatch at a terminus.

A preferred embodiment of minimally cross-hybridizing sets are those whose subunits are made up of three of the four natural nucleotides. As will be discussed more fully below, the absence of one type of nucleotide in the oligonucleotide tags permits target polynucleotides to be loaded onto solid phase supports by use of the 5'→3' exonuclease activity of a DNA polymerase. The following is an exemplary minimally cross-hybridizing set of subunits each comprising four nucleotides selected from the group consisting of A, G, and T:

TABLE II

| Word: | $w_1$ | $w_2$ | $w_3$ | $w_4$ |
|---|---|---|---|---|
| Sequence: | GATT | TGAT | TAGA | TTTG |
| Word: | $w_5$ | $w_6$ | $w_7$ | $w_8$ |
| Sequence: | GTAA | AGTA | ATGT | AAAG |

In this set, each member would form a duplex having three mismatched bases with the complement of every other member.

Further exemplary minimally cross-hybridizing sets are listed below in Table III. Clearly, additional sets can be generated by substituting different groups of nucleotides, or by using subsets of known minimally cross-hybridizing sets.

TABLE III

Exemplary Minimally Cross-Hybridizing Sets of 4-mer Subunits

| Set 1 | Set 2 | Set 3 | Set 4 | Set 5 | Set 6 |
|---|---|---|---|---|---|
| CATT | ACCC | AAAC | AAAG | AACA | AACG |
| CTAA | AGGG | ACCA | ACCA | ACAC | ACAA |
| TCAT | CACG | AGGG | AGGC | AGGG | AGGC |
| ACTA | CCGA | CACG | CACC | CAAG | CAAC |
| TACA | CGAC | CCGC | CCGG | CCGC | CCGG |
| TTTC | GAGC | CGAA | CGAA | CGCA | CGCA |
| ATCT | GCAG | GAGA | GAGA | GAGA | GAGA |
| AAAC | GGCA | GCAG | GCAC | GCCG | GCCC |
|  | AAAA | GGCC | GGCG | GGAC | GGAG |

| Set 7 | Set 8 | Set 9 | Set 10 | Set 11 | Set 12 |
|---|---|---|---|---|---|
| AAGA | AAGC | AAGG | ACAG | ACCG | ACGA |
| ACAC | ACAA | ACAA | AACA | AAAA | AAAC |
| AGCG | AGCG | AGCC | AGGC | AGGC | AGCG |
| CAAG | CAAG | CAAC | CAAC | CACC | CACA |
| CCCA | CCCC | CCCG | CCGA | CCGA | CCAG |
| CGGC | CGGA | CGGA | CGCG | CGAG | CGGC |
| GACC | GACA | GACA | GAGG | GAGG | GAGG |
| GCGG | GCGG | GCGC | GCCC | GCAC | GCCC |
| GGAA | GGAC | GGAG | GGAA | GGCA | GGAA |

The oligonucleotide tags of the invention and their complements are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are capable of specific hybridization. In some embodiments, tags may comprise naturally occurring nucleotides that permit processing or manipulation by enzymes, while the corresponding tag complements may comprise non-natural nucleotide analogs, such as peptide nucleic acids, or like compounds, that promote the formation of more stable duplexes during sorting.

When microparticles are used as supports, repertoires of oligonucleotide tags and tag complements may be generated by subunit-wise synthesis via "split and mix" techniques, e.g. as disclosed in Shortle et al. International patent application PCT/US93/03418 or Lyttle et al. Biotechniques, 19: 274–280 (1995). Briefly, the basic unit of the synthesis is a subunit of the oligonucleotide tag. Preferably, phosphoramidite chemistry is used and 3' phosphoramidite oligonucleotides are prepared for each subunit in a minimally cross-hybridizing set, e.g. for the set first listed above. there would be eight 4-mer 3'-phosphoramidites. Synthesis proceeds as disclosed by Shortle et al or in direct analogy with the techniques employed to generate diverse oligonucleotide libraries using nucleosidic monomers, e.g. as disclosed in Telenius et al, Genomics, 13: 718–725 (1992); Welsh et al, Nucleic Acids Research, 19: 5275–5279 (1991); Grothues et al, Nucleic Acids Research, 21: 1321–1322 (1993); Hartley, European patent application 90304496.4; Lam et al, Nature.

354: 82–84 (1991); Zuckerman et al, Int. J. Pept. Protein Research, 40: 498–507 (1992); and the like. Generally, these techniques simply call for the application of mixtures of the activated monomers to the growing oligonucleotide during the coupling steps. Preferably, oligonucleotide tags and tag complements are synthesized on a DNA synthesizer having a number of synthesis chambers which is greater than or equal to the number of different kinds of words used in the construction of the tags. That is, preferably there is a synthesis chamber corresponding to each type of word. In this embodiment, words are added nucleotide-by-nucleotide, such that if a word consists of five nucleotides there are five monomer couplings in each synthesis chamber. After a word is completely synthesized, the synthesis supports are removed from the chambers, mixed, and redistributed back to the chambers for the next cycle of word addition. This latter embodiment takes advantage of the high coupling yields of monomer addition, e.g. in phosphoramidite chemistries.

Double stranded forms of tags may be made by separately synthesizing the complementary strands followed by mixing under conditions that permit duplex formation. Alternatively, double stranded tags may be formed by first synthesizing a single stranded repertoire linked to a known oligonucleotide sequence that serves as a primer binding site. The second strand is then synthesized by combining the single stranded repertoire with a primer and extending with a polymerase. This latter approach is described in Oliphant et al, Gene, 44: 177–183 (1986). Such duplex tags may then be inserted into cloning vectors along with target polynucleotides for sorting and manipulation of the target polynucleotide in accordance with the invention.

When tag complements are employed that are made up of nucleotides that have enhanced binding characteristics, such as PNAs or oligonucleotide N3'→P5' phosphoramidates, sorting can be implemented through the formation of D-loops between tags comprising natural nucleotides and their PNA or phosphoramidate complements, as an alternative to the "stripping" reaction employing the 3'→5' exonuclease activity of a DNA polymerase to render a tag single stranded.

Oligonucleotide tags of the invention may range in length from 12 to 60 nucleotides or basepairs. Preferably, oligonucleotide tags range in length from 18 to 40 nucleotides or basepairs. More preferably, oligonucleotide tags range in length from 25 to 40 nucleotides or basepairs. In terms of preferred and more preferred numbers of subunits, these ranges may be expressed as follows:

TABLE IV

Numbers of Subunits in Tags in Preferred Embodiments

| Monomers in Subunit | Nucleotides in Oligonucleotide Tag | | |
|---|---|---|---|
| | (12–60) | (18–40) | (25–40) |
| 3 | 4–20 subunits | 6–13 subunits | 8–13 subunits |
| 4 | 3–15 subunits | 4–10 subunits | 6–10 subunits |
| 5 | 2–12 subunits | 3–8 subunits | 5–8 subunits |
| 6 | 2–10 subunits | 3–6 subunits | 4–6 subunits |

Most preferably, oligonucleotide tags are single stranded and specific hybridization occurs via Watson-Crick pairing with a tag complement.

Preferably, repertoires of single stranded oligonucleotide tags of the invention contain at least 100 members; more preferably, repertoires of such tags contain at least 1000 members; and most preferably, repertoires of such tags contain at least 10,000 members.

Triplex Tags

In embodiments where specific hybridization occurs via triplex formation, coding of tag sequences follows the same principles as for duplex-forming tags; however, there are further constraints on the selection of subunit sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine. and the like) in order to maximize, or otherwise regulate, triplex stability as desired in particular embodiments, e.g. Roberts et al, Proc. Natl. Acad. Sci., 88: 9397–9401 (1991); Roberts et al, Science, 258: 1463–1466 (1992); Roberts et al, Proc. Nati. Acad. Sci., 93: 4320–4325 (1996); Distefano et al, Proc. Natl. Acad. Sci., 90: 1179–1183 (1993); Mergny et al, Biochemistry, 30: 9791–9798 (1991); Cheng et al, J. Am. Chem. Soc., 114: 4465–4474 (1992); Beal and Dervan, Nucleic Acids Research, 20: 2773–2776 (1992); Beal and Dervan, J. Am. Chem. Soc., 114: 4976–4982 (1992); Giovannangeli et al, Proc. Natl. Acad. Sci., 89: 8631–8635 (1992); Moser and Dervan. Science, 238: 645–650 (1987); McShan et al, J. Biol. Chem., 267: 5712–5721 (1992); Yoon et al, Proc. Natl. Acad. Sci., 89: 3840–3844 (1992); Blume et al, Nucleic Acids Research, 20: 1777–1784 (1992); Thuong and Helene, Angew. Chem. Int. Ed. Engl. 32: 666–690 (1993); Escude et al, Proc. Natl. Acad. Sci., 93: 4365–4369 (1996); and the like. Conditions for annealing single-stranded or duplex tags to their single-stranded or duplex complements are well known, e.g. Ji et al, Anal. Chem. 65: 1323–1328 (1993); Cantor et al, U.S. Pat. No. 5,482,836; and the like. Use of triplex tags has the advantage of not requiring a "stripping" reaction with polymerase to expose the tag for annealing to its complement.

Preferably, oligonucleotide tags of the invention employing triplex hybridization are double stranded DNA and the corresponding tag complements are single stranded. More preferably, 5-methylcytosine is used in place of cytosine in the tag complements in order to broaden the range of pH stability of the triplex formed between a tag and its complement. Preferred conditions for forming triplexes are filly disclosed in the above references. Briefly, hybridization takes place in concentrated salt solution, e.g. 1.0 M NaCl, 1.0 M potassium acetate, or the like, at pH below 5.5 ( or 6.5 if 5-methylcytosine is employed). Hybridization temperature depends on the length and composition of the tag; however, for an 18–20-mer tag of longer, hybridization at room temperature is adequate. Washes may be conducted with less concentrated salt solutions, e.g. 10 mM sodium acetate, 100 mM $MgCl_2$, pH 5.8, at room temperature. Tags may be eluted from their tag complements by incubation in a similar salt solution at pH 9.0.

Minimally cross-hybridizing sets of oligonucleotide tags that form triplexes may be generated by the computer program of Appendix Ic, or similar programs. An exemplary set of double stranded 8-mer words are listed below in capital letters with the corresponding complements in small letters. Each such word differs from each of the other words in the set by three base pairs.

TABLE V

Exemplary Minimally Cross-Hybridizing Set of DoubleStranded 8-mer Tags

| | | | |
|---|---|---|---|
| 5'-AAGGAGAG | 5'-AAAGGGGA | 5'-AGAGAAGA | 5'-AGGGGGGG |
| 3'-TTCCTCTC | 3'-TTTCCCCT | 3'-TCTCTTCT | 3'-TCCCCCCC |
| 3'-ttcctctc | 3'-tttcccct | 3'-tctcttct | 3'-tcccccc |
| 5'-AAAAAAAA | 5'-AAGAGAGA | 5'-AGGAAAAG | 5'-GAAAGGAG |
| 3'-TTTTTTTT | 3'-TTCTCTCT | 3'-TCCTTTTC | 3'-CTTTCCTC |
| 3'-tttttttt | 3'-ttctctct | 3'-tccttttc | 3'-ctttcctc |
| 5'-AAAAAGGG | 5'-AGAAGAGG | 5'-AGGAAGGA | 5'-GAAGAAGG |
| 3'-TTTTTCCC | 3'-TCTTCTCC | 3'-TCCTTCCT | 3'-CTTCTTCC |
| 3'-tttttccc | 3'-tcttctcc | 3'-tccttcct | 3'-cttcttcc |
| 5'-AAAGGAAG | 5'-AGAAGGAA | 5'-AGGGGAAA | 5'-GAAGAGAA |
| 3'-TTTCCTTC | 3'-TCTTCCTT | 3'-TCCCCTTT | 3'-CTTCTCTT |
| 3'-tttccttc | 3'-tcttcctt | 3'-tccccttt | 3'-cttctctt |

TABLE VI

Repertoire Size of Various Double Stranded Tags That Form Triplexes with Their Tag Complements

| Oligo-nucleotide Word Length | Nucleotide Difference between Oligonucleotides of Minimally Cross-Hybridizing Set | Maximal Size of Minimally Cross-Hybridizing Set | Size of Repertoire with Four Words | Size of Repertoire with Five Words |
|---|---|---|---|---|
| 4 | 2 | 8 | 4096 | $3.2 \times 10^4$ |
| 6 | 3 | 8 | 4096 | $3.2 \times 10^4$ |
| 8 | 3 | 16 | $6.5 \times 10^4$ | $1.05 \times 10^6$ |
| 10 | 5 | 8 | 4096 | |
| 15 | 5 | 92 | | |
| 20 | 6 | 765 | | |
| 20 | 8 | 92 | | |
| 20 | 10 | 22 | | |

Preferably, repertoires of double stranded oligonucleotide tags of the invention contain at least 10 members; more preferably, repertoires of such tags contain at least 100 members. Preferably, words are between 4 and 8 nucleotides in length for combinatorially synthesized double stranded oligonucletide tags, and oligonucleotide tags are between 12 and 60 base pairs in length. More preferably, such tags are between 18 and 40 base pairs in length.

Solid Phase Supprts

Solid phase supports for use with the invention may have a wide variety of forms, including microparticles, beads. and membranes, slides, plates, micromachined chips, and the like. Likewise, solid phase supports of the invention may comprise a wide variety of compositions, including glass, plastic, silicon, alkanethiolate-derivatized gold, cellulose, low cross-linked and high cross-linked polystyrene, silica gel, polyamide, and the like. Preferably, either a population of discrete particles are employed such that each has a uniform coating, or population, of complementary sequences of the same tag (and no other), or a single or a few supports are employed with spatially discrete regions each containing a uniform coating, or population, of complementary sequences to the same tag (and no other). In the latter embodiment. the area of the regions may vary according to particular applications; usually, the regions range in area from several $\mu m^2$, e.g. 3–5, to several hundred $\mu m^2$, e.g. 100–500. Preferably, such regions are spatially discrete so that signals generated by events, e.g. fluorescent emissions, at adjacent regions can be resolved by the detection system being employed. In some applications, it may be desirable to have regions with uniform coatings of more than one tag complement, e.g. for simultaneous sequence analysis, or for bringing separately tagged molecules into close proximity.

Tag complements may be used with the solid phase support that they are synthesized on, or they may be separately synthesized and attached to a solid phase support for use, e.g. as disclosed by Lund et al, Nucleic Acids Research, 16: 10861–10880 (1988); Albretsen et al, Anal. Biochem., 189: 40–50 (1990); Wolf et al, Nucleic Acids Research, 15: 2911–2926 (1987); or Ghosh et al, Nucleic Acids Research, 15: 5353–5372 (1987). Preferably, tag complements are synthesized on and used with the same solid phase support, which may comprise a variety of forms and include a variety of linking moieties. Such supports may comprise microparticles or arrays, or matrices, of regions where uniform populations of tag complements are synthesized. A wide variety of microparticle supports may be used with the invention, including microparticles made of controlled pore glass (CPG), highly cross-linked polystyrene. acrylic copolymers, cellulose, nylon, dextran, latex, polyacrolein, and the like, disclosed in the following exemplary references: Meth. Enzymol., Section A, pages 11–147, vol. 44 (Academic Press, New York, 1976); U.S. Pat. Nos. 4,678, 814; 4,413,070; and 4,046;720; and Pon, Chapter 19, in Agrawal, editor, Methods in Molecular Biology, Vol. 20, (Humana Press, Totowa, N.J., 1993). Microparticle supports further include commercially available nucleoside-derivatized CPG and polystyrene beads (e.g. available from Applied Biosystems, Foster City, Calif.); derivatized magnetic beads; polystyrene grafted with polyethylene glycol (e.g., TentaGel™, Rapp Polymere, Tubingen Germany); and the like. Selection of the support characteristics, such as material, porosity, size, shape, and the like, and the type of linking moiety employed depends on the conditions under which the tags are used. For example, in applications involving successive processing with enzymes, supports and linkers that minimize steric hindrance of the enzymes and that facilitate access to substrate are preferred. Other important factors to be considered in selecting the most appropriate microparticle support include size uniformity, efficiency as a synthesis support, degree to which surface area known, and optical properties, e.g. as explain more fully below, clear smooth beads provide instrunentational advantages when handling large numbers of beads on a surface.

Exemplary linking moieties for attaching and/or synthesizing tags on microparticle surfaces are disclosed in Pon et al, Biotechniques, 6:768–775 (1988); Webb, U.S. Pat. No. 4,659,774; Barany et al, International patent application PCT/US91/06103; Brown et al, J. Chem. Soc. Commun., 1989: 891–893; Damha et al, Nucleic Acids Research, 18: 3813–3821 (1990); Beattie et al, Clinical Chemistry, 39: 719–722 (1993); Maskos and Southern, Nucleic Acids Research, 20: 1679–1684 (1 992); and the like.

As mentioned above, tag complements may also be synthesized on a single (or a few) solid phase support to form an array of regions uniformly coated with tag complements. That is, within each region in such an array the same tag complement is synthesized. Techniques for synthesizing such arays are disclosed in McGall et al, International application PCT/US93/03767; Pease et al, Proc. Natl. Acad. Sci., 91: 5022–5026 (1994); Southern and Maskos, International application PCT/GB89/01114; Maskos and Southern (cited above); Southern et al, Genomics, 13: 1008–1017 (1992); and Maskos and Southern, Nucleic Acids Research, 21: 4663–4669(1993).

Preferably, the invention is implemented with microparticles or beads uniformly coated with complements of the same tag sequence. Microparticle supports and methods of covalently or noncovalently linking oligonucleotides to their surfaces are well known, as exemplified by the following references: Beaucage and Iyer (cited above); Gait, editor, Oligonucleotide Synthesis: A Practical Approach (IRL Press, Oxford, 1984); and the references cited above. Generally, the size and shape of a microparticle is not critical; however, microparticles in the size range of a few, e.g. 1–2, to several hundred, e.g. 200–1000 $\mu$m diameter are preferable, as they facilitate the construction and manipulation of large repertoires of oligonucleotide tags with minimal reagent and sample usage.

In some preferred applications, commercially available controlled-pore glass (CPG) or polystyrene supports are employed as solid phase supports in the invention. Such supports come available with base-labile linkers and initial nucleosides attached. e.g. Applied Biosystems (Foster City, Calif.). Preferably, microparticles having pore size between 500 and 1000 angstroms are employed.

In other preferred applications, non-porous microparticles are employed for their optical properties, which may be advantageously used when tracking large numbers of microparticles on planar supports, such as a microscope slide. Particularly preferred-non-porous microparticles are the glycidal methacrylate (GMA) beads available from Bangs Laboratories (Carmel, Ind.). Such microparticles are useful in a variety of sizes and derivatized with a variety of linkage groups for synthesizing tags or tag complements. Preferably, for massively parallel manipulations of tagged microparticles, 5 $\mu$m diameter GMA beads are employed.

Attaching Tags to Polynucleotides For Sorting onto Solid Phase Supports

An important aspect of the invention is the sorting and attachment of a populations of polynucleotides, e.g. from a cDNA library, to microparticles or to separate regions on a solid phase support such that each microparticle or region has substantially only one kind of polynucleotide attached. This objective is accomplished by insuring that substantially all different polynucleotides have different tags attached. This condition, in turn, is brought about by taking a sample of the full ensemble of tag-polynucleotide conjugates for analysis. (It is acceptable that identical polynucleotides have different tags, as it merely results in the same polynucleotide being operated on or analyzed twice in two different locations.) Such sampling can be carried out either overtly—for example, by taking a small volume from a larger mixture—after the tags have been attached to the polynucleotides, it can be carried out inherently as a secondary effect of the techniques used to process the polynucleotides and tags, or sampling can be carried out both overtly and as an inherent part of processing steps.

Preferably, in constructing a cDNA library where substantially all different cDNAs have different tags, a tag repertoire is employed whose complexity, or number of distinct tags, greatly exceeds the total number of mRNAs extracted from a cell or tissue sample. Preferably, the complexity of the tag repertoire is at least 10 times that of the polynucleotide population; and more preferably, the complexity of the tag repertoire is at least 100 times that of the polynucleotide population. Below, a protocol is disclosed for cDNA library construction using a primer mixture that contains a full repertoire of exemplary 9-word tags. Such a mixture of tag-containing primers has a complexity of $8^9$, or about $1.34 \times 10^8$. As indicated by Winslow et al, Nucleic Acids Research, 19: 3251–3253 (1991), mRNA for library construction can be extracted from as few as 10–100 mammalian cells. Since a single mammalian cell contains about $5 \times 10^5$ copies of mRNA molecules of about $3.4 \times 10^4$ different kinds, by standard techniques one can isolate the mRNA from about 100 cells, or (theoretically) about $5 \times 10^7$ mRNA molecules. Comparing this number to the complexity of the primer mixture shows that without any additional steps, and even assuming that mRNAs are converted into cDNAs with perfect efficiency ( 1% efficiency or less is more accurate), the cDNA library construction protocol results in a population containing no more than 37% of the total number of different tags. That is, without any overt sampling step at all, the protocol inherently generates a sample that comprises 37%, or less, of the tag repertoire. The probability of obtaining a double under these conditions is about 5%, which is within the preferred range. With mRNA from 10 cells, the fraction of the tag repertoire sampled is reduced to only 3.7%, even assuming that all the processing steps take place at 100% efficiency. In fact, the efficiencies of the processing steps for constructing cDNA libraries are very low, a "rule of thumb" being that good library should contain about $10^8$ cDNA clones from mRNA extracted from $10^6$ mammalian cells.

Use of larger amounts of mRNA in the above protocol, or for larger amounts of polynucleotides in general, where the number of such molecules exceeds the complexity of the tag repertoire, a tag-polynucleotide conjugate mixture potentially contains every possible pairing of tags and types of mRNA or polynucleotide. In such cases, overt sampling may be implemented by removing a sample volume after a serial dilution of the starting mixture of tag-polynucleotide conjugates. The amount of dilution required depends on the amount of starting material and the efficiencies of the processing steps, which are readily estimated.

If mRNA were extracted from $10^6$ cells (which would correspond to about 0.5 $\mu$g of poly(A)$^+$RNA), and if primers were present in about 10–100 fold concentration excess—as is called for in a typical protocol, e.g. Sambrook et al, Molecular Cloning, Second Edition, page 8.61 [10 $\mu$L 1.8 kb mRNA at 1 mg/mL equals about $1.68 \times 10^{-11}$ moles and 10 $\mu$L 18-mer primer at 1 mg/mL equals about $1.68 \times 10^{-9}$ moles], then the total number of tag-polynucleotide conjugates in a cDNA library would simply be equal to or less than the starting number of mRNAs, or about $5 \times 10^{11}$ vectors containing tag-polynucleotide conjugates-again this assumes that each step in cDNA construction—first strand synthesis, second strand synthesis, ligation into a vector—occurs with perfect efficiency, which is a very conservative estimate. The actual number is significantly less.

If a sample of n tag-polynucleotide conjugates are randomly drawn from a reaction mixture—as could be effected by taking a sample volume, the probability of drawing conjugates having the same tag is described by the Poisson distribution, $P(r) = e^{-\lambda}(\lambda)^r/r$, where r is the number of conjugates having the same tag and $\lambda = np$, where p is the probability of a given tag being selected. If $n=10^6$ and $p=1/(1.34 \times 10^8)$, then $\lambda = 0.00746$ and $P(2) = 2.76 \times 10^{-5}$. Thus, a sample of one million molecules gives rise to an expected number of doubles well within the preferred range. Such a sample is readily obtained as follows: Assume that the $5 \times 10^{11}$ mRNAs are perfectly converted into $5 \times 10^{11}$ vectors with tag-cDNA conjugates as inserts and that the $5 \times 10^{11}$ vectors are in a reaction solution having a volume of 100 µl. Four 10-fold serial dilutions may be carried out by transferring 10 µl from the original solution into a vessel containing 90 µl of an appropriate buffer, such as TE. This process may be repeated for three additional dilutions to obtain a 100 µl solution containing $5\times10^5$ vector molecules per µl. A 2 µl aliquot from this solution yields $10^6$ vectors containing tag-cDNA conjugates as inserts. This sample is then amplified by straight forward transformation of a competent host cell followed by culturing.

Of course, as mentioned above, no step in the above process proceeds with perfect efficiency. In particular, when vectors are employed to amplify a sample of tag-polynucleotide conjugates, the step of transforming a host is very inefficient. Usually, no more than 1% of the vectors are taken up by the host and replicated. Thus, for such a method of amplification, even fewer dilutions would be required to obtain a sample of $10^6$ conjugates.

A repertoire of oligonucleotide tags can be conjugated to a population of polynucleotides in a number of ways, including direct enzymatic ligation, amplification, e.g. via PCR, using primers containing the tag sequences, and the like. The initial ligating step produces a very large population of tag-polynucleotide conjugates such that a single tag is generally attached to many different polynucleotides. However, as noted above, by taking a sufficiently small sample of the conjugates, the probability of obtaining "doubles," i.e. the same tag on two different polynucleotides, can be made negligible. Generally, the larger the sample the greater the probability of obtaining a double. Thus, a design trade-off exists between selecting a large sample of tag-polynucleotide conjugates—which, for example, ensures adequate coverage of a target polynucleotide in a shotgun sequencing operation or adequate representation of a rapidly changing mRNA pool, and selecting a small sample which ensures that a minimal number of doubles will be present. In most embodiments, the presence of doubles merely adds an additional source of noise or, in the case of sequencing, a minor complication in scanning and signal processing, as microparticles giving multiple fluorescent signals can simply be ignored.

As used herein, the term "substantially all" in reference to attaching tags to molecules, especially polynucleotides, is meant to reflect the statistical nature of the sampling procedure employed to obtain a population of tag-molecule conjugates essentially free of doubles. The meaning of substantially all in terms of actual percentages of tag-molecule conjugates depends on how the tags are being employed. Preferably, for nucleic acid sequencing, substantially all means that at least eighty percent of the polynucleotides have unique tags attached. More preferably, it means that at least ninety percent of the polynucleotides have unique tags attached. Still more preferably, it means that at least ninety-five percent of the polynucleotides have unique tags attached. And, most preferably, it means that at least ninety-nine percent of the polynucleotides have unique tags attached.

Preferably, when the population of polynucleotides consists of messenger RNA (mRNA), oligonucleotides tags may be attached by reverse transcribing the mRNA with a set of primers preferably containing complements of tag sequences. An exemplary set of such primers could have the following sequence (SEQ ID NO: 1):

5'-mRNA- $[A]_n$-3' $[T]_{19}$GG[W,W,W,C]$_9$AC CAGCTGATC-5'-biotin where "[W,W,W,C]$_9$" represents the sequence of an oligonucleotide tag of nine subunits of four nucleotides each and "[W,W,W,C]" represents the subunit sequences listed above, i.e. "W" represents T or A. The underlined sequences identify an optional restriction endonuclease site that can be used to release the polynucleotide from attachment to a solid phase support via the biotin, if one is employed. For the above primer, the complement attached to a microparticle could have the form:

5'-[G,W,W,W]$_9$TGG-linker-microparticle

After reverse transcription, the mRNA is removed, e.g. by RNase H digestion, and the second strand of the cDNA is synthesized using, for example, a primer of the following form (SEQ ID NO: 2):

5'-NRRGATCYNNN-3' where N is any one of A, T, G, or C; R is a purine-containing nucleotide, and Y is a pyrimidine-containing nucleotide. This particular primer creates a Bst Y1 restriction site in the resulting double stranded DNA which, together with the Sal I site, facilitates cloning into a vector with, for example, Bm HI and Xho I sites. After Bst Y1 and Sal I digestion, the exemplary conjugate would have the form:

5'-RCGACCA[C,W,W,W]$_9$GG[T]$_{19}$- cDNA -NNNR
GGT[G,W,W,W]$_9$CC[A]$_{19}$- rDNA -NNNYCTAG-5'

The polynucleotide-tag conjugates may then be manipulated using standard molecular biology techniques. For example, the above conjugate—which is actually a mixture—may be inserted into commercially available cloning vectors, e.g. Stratagene Cloning System (La Jolla, Calif.); transfected into a host, such as a commercially available host bacteria; which is then cultured to increase the number of conjugates. The cloning vectors may then be isolated using standard techniques, e.g. Sambrook et al, Molecular Cloning, Second Edition (Cold Spring Harbor Laboratory, New York, 1989). Alternatively, appropriate adaptors and primers may be employed so that the conjugate population can be increased by PCR.

Preferably, when the ligase-based method of sequencing is employed, the Bst Y1 and Sal I digested fragments are cloned into a Bam HI-/Xho I-digested vector having the following single-copy restriction sites (SEQ ID NO: 3):

5'-GA<u>GGATGC</u>CTTTAT<u>GGATCC</u>A<u>CTCGAG</u>ATCCCAATCCA-3'
    FokI        BamRI   XhoI

This adds the Fok I site which will allow initiation of the sequencing process discussed more fully below.

Tags can be conjugated to cDNAs of existing libraries by standard cloning methods. cDNAs are excised from their existing vector, isolated, and then ligated into a vector containing a repertoire of tags. Preferably, the tag-containing vector is linearized by cleaving with two restriction enzymes so that the excised cDNAs can be ligated in a predetermined orientation. The concentration of the linearized tag-containing vector is in substantial excess over that of the cDNA inserts so that ligation provides an inherent sampling of tags.

A general method for exposing the single stranded tag after amplification involves digesting a target polynucleotide-containing conjugate with the 5'→3' exonuclease activity of T4 DNA polymerase, or a like enzyme. When used in the presence of a single deoxynucleoside triphosphate, such a polymerase will cleave nucleotides from 3' recessed ends present on the non-template strand of a double stranded fragment until a complement of the single deoxynucleoside triphosphate is reached on the template strand. When such a nucleotide is reached the 5'→3' digestion effectively ceases, as the polymerase's extension activity adds nucleotides at a higher rate than the excision activity removes nucleotides. Consequently, single stranded tags constructed with three nucleotides are readily prepared for loading onto solid phase supports.

The technique may also be used to preferentially methylate interior Fok I sites of a target polynucleotide while leaving a single Fok I site at the terminus of the polynucleotide unmethylated. First, the terminal Fok I site is rendered single stranded using a polymerase with deoxycytidine triphosphate. The double stranded portion of the fragment is then methylated, after which the single stranded terminus is filled in with a DNA polymerase in the presence of all four nucleoside triphosphates, thereby regenerating the Fok I site. Clearly, this procedure can be generalized to endonucleases other than Fok I.

After the oligonucleotide tags are prepared for specific hybridization, e.g. by rendering them single stranded as described above, the polynucleotides are mixed with microparticles containing the complementary sequences of the tags under conditions that favor the formation of perfectly matched.duplexes between the tags and their complements. There is extensive guidance in the literature for creating these conditions. Exemplary references providing such guidance include Wetmur, Critical Reviews in Biochemistry and Molecular Biology, 26: 227–259 (1991); Sambrook et al, Molecular Cloning: A Laboratory Manual, 2nd Edition (Cold Spring Harbor Laboratory, New York, 1989); and the like. Preferably, the hybridization conditions are sufficiently stringent so that only perfectly matched sequences form stable duplexes. Under such conditions the polynucleotides specifically hybridized through their tags may be ligated to the complementary sequences attached to the microparticles. Finally, the microparticles are washed to remove polynucleotides with unligated and/or mismatched tags.

When CPG microparticles conventionally employed as synthesis supports are used, the density of tag complements on the microparticle surface is typically greater than that necessary for some sequencing operations. That is, in sequencing approaches that require successive treatment of the attached polynucleotides with a variety of enzymes, densely spaced polynucleotides may tend to inhibit access of the relatively bulky enzymes to the polynucleotides. In such cases, the polynucleotides are preferably mixed with the microparticles so that tag complements are present in significant excess, e.g. from 10:1 to 100:1, or greater. over the polynucleotides. This ensures that the density of polynucleotides on the microparticle surface will not be so high as to inhibit enzyme access. Preferably, the average inter-polynucleotide spacing on the microparticle surface is on the order of 30–100 nm. Guidance in selecting ratios for standard CPG supports and Ballotini beads (a type of solid glass support) is found in Maskos and Southern, Nucleic Acids Research, 20: 1679–1684 (1992). Preferably, for sequencing applications, standard CPG beads of diameter in the range of 20–50 $\mu$m are loaded with about $10^5$ polynucleotides, and GMA beads of diameter in the range of 5–10 $\mu$m are loaded with a few tens of thousand of polynucleotides, e.g. $4 \times 10^4$ to $6 \times 10^4$.

In the preferred embodiment, tag complements are synthesized on microparticles combinatorially; thus, at the end of the synthesis, one obtains a complex mixture of microparticles from which a sample is taken for loading tagged polynucleotides. The size of the sample of microparticles will depend on several factors, including the size of the repertoire of tag complements, the nature of the apparatus for used for observing loaded microparticles—e.g. its capacity, the tolerance for multiple copies of microparticles with the same tag complement (i.e. "bead doubles"), and the like. The following table provide guidance regarding microparticle sample size, microparticle diameter, and the approximate physical dimensions of a packed array of microparticles of various diameters.

| Microparticle diameter | 5 $\mu$m | 10 $\mu$m | 20 $\mu$m | 40 $\mu$m |
|---|---|---|---|---|
| Max. no. polynucleotides loaded at 1 per $10^5$ sq. angstrom | | $3 \times 10^5$ | $1.26 \times 10^6$ | $5 \times 10^6$ |
| Approx. area of monolayer of $10^6$ microparticles | .45 × .45 cm | 1 × 1 cm | 2 × 2 cm | 4 × 4 cm |

The probability that the sample of microparticles contains a given tag complement or is present in mutltiple copies is described by the poisson distribution, as indicated in the following table.

TABLE VII

| Number of microparticles in sample (as fraction of repertoire size), m | Fraction of repertoire of tag complements present in sample, $1-e^{-m}$ | Fraction of microparticles in sample with unique tag complement attached, $m(e^{-m})/2$ | Fraction of microparticles in sample carrying same tag complement as one other microparticle in sample ("bead doubles"), $m^2(e^{-m})/2$ |
|---|---|---|---|
| 1.000 | 0.63 | 0.37 | 0.18 |
| .693 | 0.50 | 0.35 | 0.12 |
| .405 | 0.33 | 0.27 | 0.05 |
| .285 | 0.25 | 0.21 | 0.03 |
| .223 | 0.20 | 0.18 | 0.02 |
| .105 | 0.10 | 0.09 | 0.005 |
| .010 | 0.01 | 0.01 | |

High Specificity Sorting and Panning

The kinetics of sorting depends on the rate of hybridization of oligonucleotide tags to their tag complements which, in turn, depends on the complexity of the tags in the hybridization reaction. Thus, a trade off exists between sorting rate and tag complexity, such that an increase in sorting rate may be achieved at the cost of reducing the complexity of the tags involved in the hybridization reaction. As explained below, the effects of this trade off may be ameliorated by "panning."

Specificity of the hybridizations may be increased by taking a sufficiently small sample so that both a high percentage of tags in the sample are unique and the nearest neighbors of substantially all the tags in a sample differ by at least two words. This latter condition may be met by taking a sample that contains a number of tag-polynucleotide conjugates that is about 0.1 percent or less of the size of the repertoire being employed. For example, if tags are constructed with eight words selected from Table II, a repertoire of $8^8$, or about $1.67 \times 10^7$, tags and tag complements are produced. In a library of tag-cDNA conjugates as described above, a 0.1 percent sample means that about 16,700 different tags are present. If this were loaded directly onto a repertoire-equivalent of microparticles, or in this example a sample of $1.67 \times 10^7$ microparticles, then only a sparse subset of the sampled microparticles would be loaded. The density of loaded microparticles can be increase—for example, for more efficient sequencing—by undertaking a "panning" step in which the sampled tag-cDNA conjugates are used to separate loaded microparticles from unloaded microparticles. Thus, in the example above, even though a "0.1 percent" sample contains only 16,700 cDNAs, the sampling and panning steps may be repeated until as many loaded microparticles as desired are accumulated.

A panning step may be implemented by providing a sample of tag-cDNA conjugates each of which contains a capture moiety at an end opposite, or distal to, the oligonucleotide tag. Preferably, the capture moiety is of a type which can be released from the tag-cDNA conjugates, so that the tag-cDNA conjugates can be sequenced with a single-base sequencing method. Such moieties may comprise biotin, digoxigenin, or like ligands, a triplex binding region, or the like. Preferably, such a capture moiety comprises a biotin component. Biotin may be attached to tag-cDNA conjugates by a number of standard techniques. If appropriate adapters containing PCR primer binding sites are attached to tag-cDNA conjugates, biotin may be attached by using a biotinylated primer in an amplification after sampling. Alternatively, if the tag-cDNA conjugates are inserts of cloning vectors, biotin may be attached after excising the tag-cDNA conjugates by digestion with an appropriate restriction enzyme followed by isolation and filling in a protruding strand distal to the tags with a DNA polymerase in the presence of biotinylated uridine triphosphate.

After a tag-cDNA conjugate is captured, it may be released from the biotin moiety in a number of ways, such as by a chemical linkage that is cleaved by reduction, e.g. Herman et al, Anal. Biochem., 156: 48–55 (1986), or that is cleaved photochemically, e.g. Olejnik et al, Nucleic Acids Research, 24: 361–366 (1996), or that is cleaved enzymatically by introducing a restriction site in the PCR primer. The latter embodiment can be exemplified by considering the library of tag-polynucleotide conjugates described above:

5'-RCGACCA[C,W,W,W]$_9$GG[T]$_{19}$-cDNA-NNNR (SEQ ID NO:7)

GGT[G,W,W,W]$_9$CC[A]$_{19}$-rDNA-NNNYCTAG-5'(SEQ ID NO:8)

The following adapters may be ligated to the ends of these fragments to permit amplification by PCR:

```
5'- XXXXXXXXXXXXXXXXXXXX              SEQ ID NO:9
    XXXXXXXXXXXXXXXXXXXXYGAT

Right Adapter

GATCZZACTAGTZZZZZZZZZZZZ-3'           SEQ ID NO:10
    ZZTGATCAZZZZZZZZZZZZ

Left Adapter

ZZTGATCAZZZZZZZZZZZZ-5'-biotin

Left Primer
``` where "ACTAGT" is a Spe I recognition site (which leaves a staggered cleavage ready for single base sequencing), and the X's and Z's are nucleotides selected so that the annealing and dissociation temperatures of the respective primers are approximately the same. After ligation of the adapters and amplification by PCR using the biotinylated primer, the tags of the conjugates are rendered single stranded by the exonuclease activity of T4 DNA polymerase and conjugates are combined with a sample of microparticles, e.g. a repertoire equivalent, with tag complements attached. After annealing under stringent conditions (to minimize mis-attachment of tags), the conjugates are preferably ligated to their tag complements and the loaded microparticles are separated from the unloaded microparticles by capture with avidinated magnetic beads, or like capture technique.

Returning to the example, this process results in the accumulation of about 10,500 (=16,700×0.63) loaded microparticles with different tags, which may be released from the magnetic beads by cleavage with Spe I. By repeating this process 40–50 times with new samples of microparticles and tag-cDNA conjugates, 4–5×10$^5$ cDNAs can be accumulated by pooling the released microparticles. The pooled microparticles may then be simultaneously sequenced by a single-base sequencing technique.

Determining how many times to repeat the sampling and panning steps—or more generally, determining how many cDNAs to analyze, depends on one's objective. If the objective is to monitor the changes in abundance of relatively common sequences, e.g. making up 5% or more of a population, then relatively small samples, i.e. a small fraction of the total population size, may allow statistically significant estimates of relative abundances. On the other hand, if one seeks to monitor the abundances of rare sequences, e.g. making up 0.1% or less of a population, then large samples are required. Generally, there is a direct relationship between sample size and the reliability of the estimates of relative abundances based on the sample. There is extensive guidance in the literature on determining appropriate sample sizes for making reliable statistical estimates, e.g. Koller et al, Nucleic Acids Research, 23:185–191 (1994); Good, Biometrika, 40: 16–264 (1953); Bunge et al, J. Am. Stat. Assoc., 88: 364–373 (1993); and the like. Preferably, for monitoring changes in gene expression based on the analysis of a series of cDNA libraries containing 10$^5$ to 10$^8$ independent clones of 3.0–3.5×10$^4$ different sequences, a sample of at least 10$^4$ sequences are accumulated for analysis of each library. More preferably, a sample of at least 10$^5$ sequences are accumulated for the analysis of each library; and most preferably, a sample of at least 5×10$^5$ sequences are accumulated for the analysis of each library. Alternatively, the number of sequences sampled is preferably sufficient to estimate the relative abundance of a sequence present at a frequency within the range of 0.1% to 5% with a 95% confidence limit no larger than 0.1% of the population size.

Single Base DNA Sequencing

The present invention can be employed with conventional methods of DNA sequencing, e.g. as disclosed by Hultman et al, Nucleic Acids Research, 17: 4937–4946 (1989). However, for parallel, or simultaneous, sequencing of multiple polynucleotides, a DNA sequencing methodology is preferred that requires neither electrophoretic separation of closely sized DNA fragments nor analysis of cleaved nucleotides by a separate analytical procedure, as in peptide sequencing. Preferably, the methodology permits the stepwise identification of nucleotides, usually one at a time, in a sequence through successive cycles of treatment and detection. Such methodologies are referred to herein as "single base" sequencing methods. Single base approaches are disclosed in the following references: Cheeseman, U.S. Pat. No. 5,302,509; Tsien et al, International application WO 91/06678; Rosenthal et al, International application WO 93/21340; Canard et al, Gene, 148: 1–6 (1994); and Metzker et al, Nucleic Acids Research, 22: 4259–4267 (1994).

A "single base" method of DNA sequencing which is suitable for use with the present invention and which requires no electrophoretic separation of DNA fragments is described in International application PCT/US95/03678. Briefly, the method comprises the following steps: (a) ligating a probe to an end of the polynucleotide having a protruding strand to form a ligated complex, the probe having a complementary protruding strand to that of the polynucleotide and the probe having a nuclease recognition site; (b) removing unligated probe from the ligated complex; (c) identifying one or more nucleotides in the protruding strand of the polynucleotide by the identity of the ligated probe; (d) cleaving the ligated complex with a nuclease; and (e) repeating steps (a) through (d) until the nucleotide sequence of the polynucleotide. or a portion thereof, is determined.

A single signal generating moiety, such as a single fluorescent dye, may be employed when sequencing several different target polynucleotides attached to different spatially addressable solid phase supports, such as fixed microparticles, in a parallel sequencing operation. This may be accomplished by providing four sets of probes that are applied sequentially to the plurality of target polynucleotides on the different microparticles. An exemplary set of such probes are shown below:

| Set 1 | Set 2 | Set 3 | Set 4 |
|---|---|---|---|
| ANNNN...NN | dANNNN...NN | dANNNN...NN | dANNNN...NN |
| N...NNTT...T* | d N...NNTT...T | N...NNTT...T | N...NNTT...T |
| dCNNNN...NN | CNNNN...NN | dCNNNN...NN | dCNNNN...NN |
| N...NNTT...T | N...NNTT...T* | N...NNTT...T | N...NNTT...T |
| dGNNNN...NN | dGNNNN...NN | GNNNN...NN | dGNNNN...NN |
| N...NNTT...T | N...NNTT...T | N...NNTT...T* | N...NNTT...T |
| dTNNNN...NN | dTNNNN...NN | dTNNNN.. .NN | TNNNN...NN |
| N...NNTT...T | N...NNTT...T | N...NNTT...T | N...NNTT...T* | where each of the listed probes represents a mixture of $4^3=64$ oligonucleotides such that the identity of the 3' terminal nucleotide of the top strand is fixed and the other positions in the protruding strand are filled by every 3-mer permutation of nucleotides, or complexity reducing analogs. The listed probes are also shown with a single stranded poly-T tail with a signal generating moiety attached to the terminal thymidine, shown as "T*". The "d" on the unlabeled probes designates a ligation-blocking moiety or absense of 3'-hydroxyl, which prevents unlabeled probes from being ligated. Preferably, such 3'-terminal nucleotides are dideoxynucleotides. In this embodiment, the probes of set 1 are first applied to the plurality of target polynucleotides and treated with a ligase so that target polynucleotides having a thymidine complementary to the 3' terminal adenosine of the labeled probes are ligated. The unlabeled probes are simultaneously applied to minimize inappropriate ligations. The locations of the target polynucleotides that form ligated complexes with probes terminating in "A" are identified by the signal generated by the label carried on the probe. After washing and cleavage, the probes of set 2 are applied. In this case, target polynucleotides forming ligated complexes with probes terminating in "C" are identified by location. Similarly, the probes of sets 3 and 4 are applied and locations of positive signals identified. This process of sequentially applying the four sets of probes continues until the desired number of nucleotides are identified on the target polynucleotides. Clearly, one of ordinary skill could construct similar sets of probes that could have many variations, such as having protruding strands of different lengths, different moieties to block ligation of unlabeled probes, different means for labeling probes, and the like.

Apparatus for Sequencing Populations of Polynucleotides

An objective of the invention is to sort identical molecules, particularly polynucleotides, onto the surfaces of microparticles by the specific hybridization of tags and their complements. Once such sorting has taken place, the presence of the molecules or operations performed on them can be detected in a number of ways depending on the nature of the tagged molecule, whether microparticles are detected separately or in "batches," whether repeated measurements are desired, and the like. Typically, the sorted molecules are exposed to ligands for binding, e.g. in drug development, or are subjected chemical or enzymatic processes, e.g. in polynucleotide sequencing. In both of these uses it is often desirable to simultaneously observe signals corresponding to such events or processes on large numbers of microparticles. Microparticles carrying sorted molecules (referred to herein as "loaded" microparticles) lend themselves to such large scale parallel operations, e.g. as demonstrated by Lam et al (cited above).

Preferably, whenever light-generating signals, e.g. chemiluminescent, fluorescent, or the like, are employed to detect events or processes, loaded microparticles are spread on a planar substrate, e.g. a glass slide, for examination with a scanning system, such as described in International patent applications PCT/US91/09217, PCT/NL90/00081, and PCT/US95/01886. The scanning system should be able to reproducibly scan the substrate and to define the positions of each microparticle in a predetermined region by way of a coordinate system. In polynucleotide sequencing applications, it is important that the positional identification of microparticles be repeatable in successive scan steps.

Such scanning systems may be constructed from commercially available components, e.g. x-y translation table controlled by a digital computer used with a detection system comprising one or more photomultiplier tubes, or alternatively, a CCD array, and appropriate optics, e.g. for exciting, collecting, and sorting fluorescent signals. In some embodiments a confocal optical system may be desirable. An exemplary scanning system suitable for use in four-color sequencing is illustrated diagrammatically in FIG. 5. Substrate 300, e.g. a microscope slide with fixed microparticles, is placed on x-y translation table 302, which is connected to and controlled by an appropriately programmed digital computer 304 which may be any of a variety of commercially available personal computers, e.g. 486-based machines or PowerPC model 7100 or 8100 available form Apple Computer (Cupertino, Calif.). Computer software for table translation and data collection functions can be provided by commercially available laboratory software, such as Lab Windows, available from National Instruments.

Figure 2:
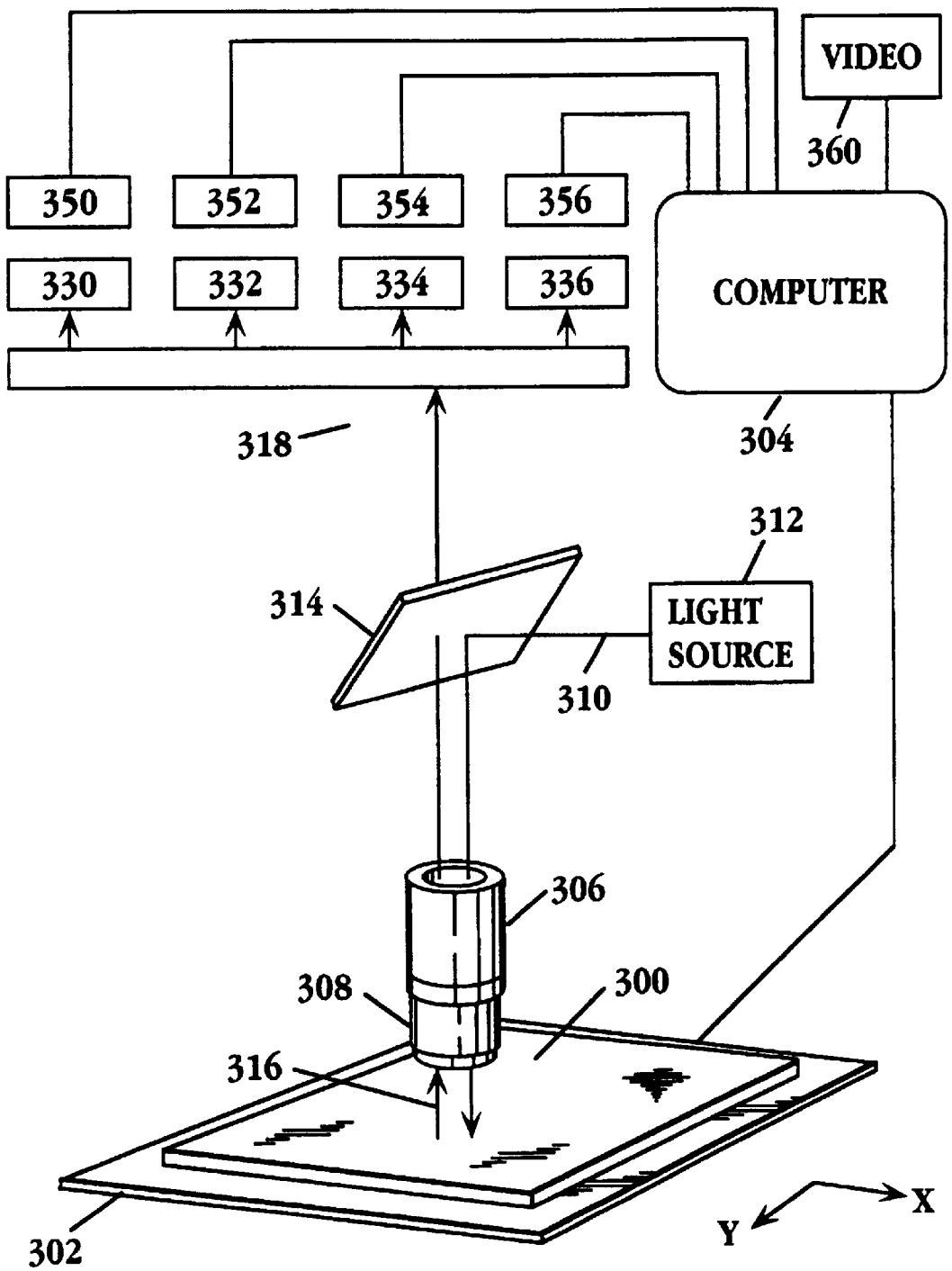
FIG. 2 diagrammatically illustrates an apparatus for carrying out polynucleotide sequencing in accordance with the invention.

Substrate 300 and table 302 are operationally associated with microscope 306 having one or more objective lenses 308 which are capable of collecting and delivering light to microparticles fixed to substrate 300. Excitation beam 310 from light source 312, which is preferably a laser, is directed to beam splitter 314, e.g. a dichroic mirror, which re-directs the beam through microscope 306 and objective lens 308 which, in tun, focuses the beam onto substrate 300. Lens 308 collects fluorescence 316 emitted from the microparticles and directs it through beam splitter 314 to signal distribution optics 318 which, in turn, directs fluorescence to one or more suitable opto-electronic devices for converting some fluorescence characteristic. e.g. intensity, lifetime, or the like, to an electrical signal. Signal distribution optics 318 may comprise a variety of components standard in the art, such as bandpass filters, fiber optics, rotating mirrors, fixed position mirrors and lenses, diffraction gratings, and the like. As illustrated in FIG. 2, signal distribution optics 318 directs fluorescence 316 to four separate photomultiplier tubes, 330, 332, 334, and 336, whose output is then directed to pre-amps and photon counters 350, 352, 354, and 356. The output of the photon counters is collected by computer 304, where it can be stored, analyzed, and viewed on video 360. Alternatively, signal distribution optics 318 could be a diffraction grating which directs fluorescent signal 318 onto a CCD array.

The stability and reproducibility of the positional localization in scanning will determine, to a large extent, the resolution for separating closely spaced microparticles. Preferably, the scanning systems should be capable of resolving closely spaced microparticles, e.g. separated by a particle diameter or less. Thus, for most applications, e.g. using CPG microparticles, the scanning system should at least have the capability of resolving objects on the order of 10–100 μm. Even higher resolution may be desirable in some embodiments, but with increase resolution, the time required to fully scan a substrate will increase; thus. in some embodiments a compromise may have to be made between speed and resolution. Increases in scanning time can be achieved by a system which only scans positions where microparticles are known to be located, e.g from an initial full scan. Preferably, microparticle size and scanning system resolution are selected to permit resolution of fluorescently labeled microparticles randomly disposed on a plane at a density between about ten thousand to one hundred thousand microparticles per $cm^2$.

In sequencing applications, loaded microparticles can be fixed to the surface of a substrate in variety of ways. The fixation should be strong enough to allow the microparticles to undergo successive cycles of reagent exposure and washing without significant loss. When the substrate is glass, its surface may be derivatized with an alkylamino linker using commercially available reagents, e.g. Pierce Chemical, which in turn may be cross-linked to avidin, again using conventional chemistries, to form an avidinated surface. Biotin moieties can be introduced to the loaded microparticles in a number of ways. For example, a fraction, e.g. 10–15 percent, of the cloning vectors used to attach tags to polynucleotides are engineered to contain a unique restriction site (providing sticky ends on digestion) immediately adjacent to the polynucleotide insert at an end of the polynucleotide opposite of the tag. The site is excised with the polynucleotide and tag for loading onto microparticles. After loading, about 10–15 percent of the loaded polynucleotides will possess the unique restriction site distal from the microparticle surface. After digestion with the associated restriction endonuclease, an appropriate double stranded adaptor containing a biotin moiety is ligated to the sticky end. The resulting microparticles are then spread on the avidinated glass surface where they become fixed via the biotin-avidin linkages.

Alternatively and preferably when sequencing by ligation is employed, in the initial ligation step a mixture of probes is applied to the loaded microparticle: a fraction of the probes contain a type IIs restriction recognition site, as required by the sequencing method, and a fraction of the probes have no such recognition site, but instead contain a biotin moiety at its non-ligating end. Preferably, the mixture comprises about 10–15 percent of the biotinylated probe.

In still another alternative, when DNA-loaded microparticles are applied to a glass substrate, the DNA may non-specifically adsorb to the glass surface upon several hours, e.g. 24 hours, incubation to create a bond sufficiently strong to permit repeated exposures to reagents and washes without significant loss of microparticles. Preferably, such a glass substrate is a flow cell, which may comprise a channel etched in a glass slide. Preferably, such a channel is closed so that fluids may be pumped through it and has a depth sufficiently close to the diameter of the microparticles so that a monolayer of microparticles is trapped within a defined observation region.

Identification of Novel Polynucleotides in cDNA Libraries

Novel polynucleotides in a cDNA library can be identified by constructing a library of cDNA molecules attached to microparticles, as described above. A large fraction of the library, or even the entire library, can then be partially sequenced in parallel. After isolation of mRNA, and perhaps normalization of the population as taught by Soares et al, Proc. Natl. Acad. Sci., 91: 9228–9232 (1994), or like references, the following primer may by hybridized to the polyA tails for first strand synthesis with a reverse transcriptase using conventional protocols (SEQ ID NO: 1):

5'-mRNA-[A]$_n$-3'[T]$_{19}$-[primer site]-GG[W,W,W,C] 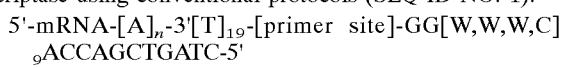$_9$ACCAGCTGATC-5' where [W,W,W,C]$_9$ represents a tag as described above, "ACCAGCTGATC" is an optional sequence forming a restriction site in double stranded form, and "primer site" is a sequence common to all members of the library that is later used as a primer binding site for amplifying polynucleotides of interest by PCR.

After reverse transcription and second strand synthesis by conventional techniques, the double stranded fragments are inserted into a cloning vector as described above and amplified. The amplified library is then sampled and the sample amplified. The cloning vectors from the amplified sample are isolated, and the tagged cDNA fragments excised and purified. After rendering the tag single stranded with a polymerase as described above, the fragments are methylated and sorted onto microparticles in accordance with the invention. Preferably, as described above, the cloning vector is constructed so that the tagged cDNAs can be excised with an endonuclease, such as Fok I, that will allow immediate sequencing by the preferred single base method after sorting and ligation to microparticles.

Stepwise sequencing is then carried out simultaneously on the whole library, or one or more large fractions of the library, in accordance with the invention until a sufficient number of nucleotides are identified on each cDNA for unique representation in the genome of the organism from which the library is derived. For example, if the library is derived from mammalian mRNA then a randomly selected sequence 14–15 nucleotides long is expected to have unique representation among the 2–3 thousand megabases of the typical mammalian genome. Of course identification of far fewer nucleotides would be sufficient for unique representation in a library derived from bacteria, or other lower organisms. Preferably, at least 20–30 nucleotides are identified to ensure unique representation and to permit construction of a suitable primer as described below. The tabulated sequences may then be compared to known sequences to identify unique cDNAs.

Unique cDNAs are then isolated by conventional techniques, e.g. constructing a probe from the PCR amplicon produced with primers directed to the prime site and the portion of the cDNA whose sequence was determined. The probe may then be used to identify the cDNA in a library using a conventional screening protocol.

The above method for identifying new cDNAs may also be used to fingerprint mRNA populations, either in isolated measurements or in the context of a dynamically changing population. Partial sequence information is obtained simultaneously from a large sample, e.g. ten to a hundred thousand, or more, of cDNAs attached to separate microparticles as described in the above method.

EXAMPLE 1

Construction of a Tag Library

An exemplary tag library is constructed as follows to form the chemically synthesized 9-word tags of nucleotides A, G, and T defined by the formula:

3'-TGGC-[$^4$(A,G,T)$_9$]-CCCCp where "[$^4$(A,G,T)$_9$]" indicates a tag mixture where each tag consists of nine 4-mer words of A, G, and T; and "p" indicate a 5' phosphate. This mixture is ligated to the following right and left primer binding regions (SEQ ID NO: 4 and SEQ ID NO 5):

```
5'- AGTGGCTGGGCATCGGACCG    5'- GGGGCCCAGTCAGCGTCGAT
    TCACCGACCCGTAGCCp           GGGTCAGTCGCAGCTA

LEFT                        RIGHT
```

The right and left primer binding regions are ligated to the above tag mixture, after which the single stranded portion of the ligated structure is filled with DNA polymerase then mixed with the right and left primers indicated below and amplified to give a tag library (SEQ ID NO: 6).

region of the right primer binding region indicates recognition sites for Bsp 120I, Apa I, and Eco O 109I, and a cleavage site for Hga I. The right-most underlined region of the right primer binding region indicates the recognition site for Hga I. Optionally, the right or left primers may be synthesized with a biotin attached (using conventional reagents, e.g. available from Clontech Laboratories, Palo Alto, Calif.) to facilitate purification after amplification and/or cleavage.

EXAMPLE 2

Changes in Gene Expression Profiles in Liver Tissue of Rats Exposed to Various Xenobiotic Agents In this experiment, to test the capability of the method of the invention to detect genes induced as a result of exposure to xenobiotic compounds, the gene expression profile of rat liver tissue is examined following administration of several compounds known to induce the expression of cytochrome P-450 isoenzymes. The results obtained from the method of the invention are compared to results obtained from reverse transcriptase PCR measurements and immunochemical measurements of the cytochrome P-450 isoenzymes. Protocols and materials for the latter assays are described in Morris et al, Biochemical Pharmacology, 52: 781–792 (1996).

Male Sprague-Dawley rats between the ages of 6 and 8 weeks and weighing 200–300 g are used, and food and water are available to the animals ad lib. Test compounds are phenobarbital (PB), metyrapone (MET), dexamethasone (DEX), clofibrate (CLO), corn oil (CO), and β-naphthoflavone (BNF), and are available from Sigma Chemical Co. (St. Louis, Mo.). Antibodies against specific P-450 enzymes are available from the following sources: rabbit anti-rat CYP3A1 from Human Biologics, Inc. (Phoenix, Ariz.); goat anti-rat CYP4A1 from Daiichi Pure Chemicals Co. (Tokyo, Japan); monoclonal mouse anti-rat CYP1A1, monoclonal mouse anti-rat CYP2C11, goat anti-rat CYP2E1, and monoclonal mouse anti-rat CYP2B1 from Oxford Biochemical Research, Inc. (Oxford, Mich.). Secondary antibodies (goat anti-rabbit IgG, rabbit anti-goat IgG and goat anti-mouse IgG) are available from Jackson ImmunoResearch Laboratories (West Grove, Pa.).

Animals are administered either PB (100 mg/kg), BNF (100 mg/kg), MET (100 mg/kg), DEX (100 mg/kg), or CLO (250 mg/kg) for 4 consecutive days via intraperitoneal injection following a dosing regimen similar to that described by Wang et al, Arch. Biochem. Biophys. 290: 355–361 (1991). Animals treated with H$_2$O and CO are used as controls. Two hours following the last injection (day 4), animals are killed, and the livers are removed. Livers are immediately frozen and stored at −70° C.

```
    Left Primer

5'- AGTGGCTGGGCATCGGACCG

5'- AGTGGCTGGGCATCGGACCG-  [⁴(A,G,T)₉]-GGGGCCCAGTCAGCGTCGAT
    TCACCGACCCGTAGCCTGGC-  [⁴(A,G,T)₉]-CCCCGGGTCAGTCGCAGCTA

CCCCGGGTCAGTCGCAGCTA-5'

Right Primer
```

The underlined portion of the left primer binding region indicates a Rsr II recognition site. The left-most underlined Total RNA is prepared from frozen liver tissue using a modification of the method described by Xie et al, Biotechniques, 11: 326–327 (1991). Approximately 100–200 mg of liver tissue is homogenized in the RNA extraction buffer described by Xie et al to isolate total RNA. The resulting RNA is reconstituted in diethylpyrocarbonate-treated water, quantified spectrophotometrically at 260 nm, and adjusted to a concentration of 100 µg/ml. Total RNA is stored in diethylpyrocarbonate-treated water for up to 1 year at −70° C. without any apparent degradation. RT-PCR and sequencing are performed on samples from these preparations.

For sequencing, samples of RNA corresponding to about 0.5 µg of poly(A)$^+$ RNA are used to construct libraries of tag-cDNA conjugates following the protocol described in the section entitled "Attaching Tags to Polynucleotides for Sorting onto Solid Phase Supports," with the following exception: the tag repertoire is constructed from six 4-nucleotide words from Table II. Thus, the complexity of the repertoire is $8^6$ or about $2.6 \times 10^5$. For each tag-cDNA conjugate library constructed, ten samples of about ten thousand clones are taken for amplification and sorting. Each of the amplified samples is separately applied to a fixed monolayer of about $10^6$ 10 µm diameter GMA beads containing tag complements. That is, the "sample" of tag complements in the GMA bead population on each monolayer is about four fold the total size of the repertoire, thus ensuring there is a high probability that each of the sampled tag-cDNA conjugates will find its tag complement on the monolayer. After the oligonucleotide tags of the amplified samples are rendered single stranded as described above, the tag-cDNA conjugates of the samples are separately applied to the monolayers under conditions that permit specific hybridization only between oligonucleotide tags and tag complements forming perfectly matched duplexes. Concentrations of the amplified samples and hybridization times are selected to permit the loading of about $5 \times 10^4$ to $2 \times 10^5$ tag-cDNA conjugates on each bead where perfect matches occur. After ligation, 9–12 nucleotide portions of the attached cDNAs are determined in parallel by the single base sequencing technique described by Brenner in International patent application PCT/US95/03678. Frequency distributions for the gene expression profiles are assembled from the sequence information obtained from each of the ten samples.

RT-PCRs of selected mRNAs corresponding to cytochrome P-450 genes and the constitutively expressed cyclophilin gene are carried out as described in Morris et al (cited above). Briefly, a 20 µL reaction mixture is prepared containing 1×reverse transcriptase buffer (Gibco BRL), 10 nM dithiothreitol, 0.5 nM dNTPs, 2.5 µM oligo d(T)$_{15}$ primer, 40 units RNasin (Promega, Madison, Wis.), 200 units RNase H-reverse transcriptase (Gibco BRL), and 400 ng of total RNA (in diethylpyrocarbonate-treated water). The reaction is incubated for 1 hour at 37° C. followed by inactivation of the enzyme at 95° C. for 5 min. The resulting cDNA is stored at −20° C. until used. For PCR amplification of cDNA, a 10 µL reaction mixture is prepared containing 10×polymerase reaction buffer, 2 mM MgCl$_2$, 1 unit Taq DNA polymerase (Perkin-Elmer, Norwalk, Conn.), 20 ng cDNA, and 200 nM concentration of the 5' and 3' specific PCR primers of the sequences described in Morris et al (cited above). PCRs are carried out in a Perkin-Elmer 9600 thermal cycler for 23 cycles using melting, annealing, and extension conditions of 94° C. for 30 sec., 56° C. for 1 min., and 72° C. for 1 min., respectively. Amplified cDNA products are separated by PAGE using 5% native gels. Bands are detected by staining with ethidium bromide.

Western blots of the liver proteins are carried out using standard protocols after separation by SDS-PAGE. Briefly, proteins are separated on 10% SDS-PAGE gels under reducing conditions and immunoblotted for detection of P-450 isoenzymes using a modification of the methods described in Harris et al, Proc. Natl. Acad. Sci., 88: 1407–1410 (1991). Proteins are loaded at 50 µg/lane and resolved under constant current (250 V) for approximately 4 hours at 2° C. Proteins are transferred to nitrocellulose membranes (Bio-Rad, Hercules, Calif.) in 15 mM Tris buffer containing 120 mM glycine and 20% (v/v) methanol. The nitrocellulose membranes are blocked with 2.5% BSA and immunoblotted for P-450 isoenzymes using primary monoclonal and polyclonal antibodies and secondary alkaline phosphatase conjugated anti-IgG. Inununoblots are developed with the Bio-Rad alkaline phosphatase substrate kit.

The three types of measurements of P-450 isoenzyme induction showed substantial agreement.

APPENDIX Ia

Exemplary computer program for generating
minimally cross hybridizing sets
(single stranded tag/single stranded tag complement)

```
Program minxh
c
c
c
           integer*2 sub1(6),mset1(1000,6),mset2(1000,6)
           dimension nbase (6)
c
c
           write(*,*)'ENTER SUBUNIT LENGTH'
           read(*,100)nsub
100        format(il)
           open(1,file='sub4.dat',form='formatted',status='new')
c
c
           nset=0
           do 7000 ml=1,3
             do 7000 m2=1,3
               do 7000 m3=1,3
                 do 7000 m4=1,3
                   sub1(1)=m1
                   sub1(2)=m2
                   sub1(3)=m3
                   sub1(4)=m4
c
c
           ndiff=3
c
c
c                Generate set of subunits differing from
                 sub1 by at least ndiff nucleotides.
                 Save in mset1.
c
c
c
           jj=1
           do 900 j=1,nsub
900          mset1(1,j)=sub1(j)
c
c
           do 1000 k1=1,3
             do 1000 k2=1,3
               do 1000 k3=1,3
                 do 1000 k4=1,3
c
c
                   nbase(1)=k1
                   nbase(2)=k2
                   nbase(3)=k3
                   nbase(4)=k4
c
           n=0
           do 1200 j=1,nsub
             if(sub1(j).eq.1 .and. nbase(j).ne.1 .or.
1              sub1(j).eq.2 .and. nbase(j).ne.2 .or.
3              sub1(j).eq.3 .and. nbase(j).ne.3) then
```

APPENDIX Ia-continued

Exemplary computer program for generating
minimally cross hybridizing sets
(single stranded tag/single stranded tag complement)

```
              n=n+1
              endif
1200  continue
c
c
       if(n.ge.ndiff) then
c
c                        If number of mismatches
c                        is greater than or equal
c                        to ndiff then record
c                        subunit in matrix mset
c
       jj=jj+1
           do 1100 i=1,nsub
1100         mset1(jj,i)=nbase(i)
       endif
c
c
1000  continue
c
c
       do 1325 j2=1,nsub
       mset2(1,j2)=mset1(1,j2)
1325  mset2(2,j2)=mset1(2,j2)
c
c                        compare subunit 2 from
c                        mset1 with each successive
c                        subunit in mset1, i.e. 3,
c                        4,5, . . . etc. Save those
c                        with mismatches .ge. ndiff
c                        in matrix mset2 starting at
c                        position 2.
c                          Next transfer contents
c                        of mset2 into mset1 and
c                        start
c                        comparisons again this time
c                        starting with subunit 3.
c                        Continue until all subunits
c                        undergo the comparisons.
c
c
       npass=0
c
c
1700  continue
       kk=npass+2
       npass=npass+1
c
c
       do 1500 m=npass+2,jj
       n=0
           do 1600 j=1,nsub
           if(mset1(npass+1,j).eq.1.and.mset1(m,j).ne.1.or.
2          mset1(npass+1,j).eq.2.and.mset1(m,j).ne.2.or.
2          mset1(npass+1,j).eq.3.and.mset1(m,j).ne.3) then
           n=n+1
           endif
1600       continue
           if(n.ge.ndiff) then
           kk=kk+1
              do 1625 i=1,nsub
1625          mset2(kk,i)=mset1(m,i)
           endif
1500  continue
c                        kk is the number of subunits
c                        stored in mset2
c
c                        Transfer contents of mset2
c                        into mset1 for next pass.
c
           do 2000 k=1,kk
              do 2000 m=1,nsub
2000          mset1(k,m)=mset2(k,m)
```

APPENDIX Ia-continued

Exemplary computer program for generating
minimally cross hybridizing sets
(single stranded tag/single stranded tag complement)

```
       if(kk.lt.jj) then
           jj=kk
           goto 1700
       endif
c
c
       nset=nset+1
       write(1,7009)
7009  format(/)
       do 7008 k=1,kk
7008       write(1,7010)(mset1(k,m),m=1,nsub)
7010  format(4i1)
       write (*,*)
       write(*,120) kk,nset
120   format(1x, 'Subunits in set=',i5,2x, 'Set No=',i5)
7000  continue
       close (1)
c
c end
c      ********************
c      ********************
```

APPENDIX Ib

Exemplary computer program for generating
minimally cross hybridizing sets
(single stranded tag/single stranded tag complement)

```
Program tagN
c
c
c      Program tagN generates minimally cross-hybridizing
c      sets of subunits given i) N--subunit length, and ii)
c      an initial subunit sequence. tagN assumes that only
c      3 of the four natural nucleotides are used in the tags.
c
c
       character*1 sub1(20)
       integer*2 mset(10000, 20), nbase(20)
c
c
       write(*,*)'ENTER SUBUNIT LENGTH'
       read(*,100)nsub
100   format(i2)
c
       write(*,*)'ENTER SUBUNIT SEQUENCE'
       read(*,110)(sub1(k),k=1,nsub)
110   format(20a1)
c
       ndiff=10
c
c             Let a=1 c=2 g=3 & t=4
       do 800 kk=1,nsub
       if(sub1(kk).eq.'a') then
           mset(1, kk)=1
           endif
              if(sub1(kk).eq.'c') then
              mset (i, kk)=2
              endif
                 if(sub1(kk).eq.'g') then
                 mset(1,kk)=3
                 endif
                    if(sub1(kk).eq.'t') then
                    mset (1,kk)=4
                    endif
800   continue
c
       jj=1
c
```

APPENDIX Ib-continued

Exemplary computer program for generating
minimally cross hybridizing sets
(single stranded tag/single stranded tag complement)

```
c
            do 1000 k1=1,3
              do 1000 k2=1,3
                do 1000 k3=1,3
                  do 1000 k4=1,3
                    do 1000 k5=1,3
                      do 1000 k6=1,3
                        do 1000 k7=1,3
                          do 1000 k8=1,3
                            do 1000 k9=1,3
                              do 1000 k10=1,3
          do 1000 k11=1,3
            do 1000 k12=1,3
              do 1010 k13=1,3
                do 1000 k14=1,3
                  do 1000 k15=1,3
                    do 1000 k16=1,3
                      do 1000 k17=1,3
                        do 1000 k18=1,3
                          do 1000 k19=1,3
                            do 1000 k20=1,3
c
                  nbase(1)=k1
                  nbase(2)=k2
                  nbase(3)=k3
                  nbase(4)=k4
                  nbase(5)=k5
                  nbase(6)=k6
                  nbase(7)=k7
                  nbase(8)=k8
                  nbase(9)=k9
                  nbase(10)=k10
                  nbase(11)=k11
                  nbase(12)=k12
                  nbase(13)=k13
                  nbase(14)=k14
                  nbase(15)=k15
                  nbase(16)=k16
                  nbase(17)=k17
                  nbase(18)=k18
                  nbase(19)=k19
                  nbase(20)=k20
c
            do 1250 nn=1,jj
c
              n=0
              do 1200 j=1,nsub
                if(mset(nn,j).eq.1 .and. nbase(j).ne.1 .or.
1                  mset(nn,j) .eq.2 .and. nbase(j) .ne.2 .or.
2                  mset(nn,j) .eq.3 .and. nbase(j) .ne.3 .or.
3                  mset(nn,j) .eq.4 .and. nbase(j) .ne.4) then
                    n=n+1
                endif
1200          continue
c
              if(n.lt.ndiff) then
                goto 1000
              endif
1250        continue
c
            jj=jj+1
            write(*,130)(nbase(i),i=1,nsub),jj
            do 1100 i=1,nsub
              mset (jj, i)=nbase (i)
1100        continue
c
1000    continue
c
            jj=jj+1
            write(*,130)(nbase(i),i=1,nsub),jj
            do 1100 i=1,nsub
              mset(jj,i)=nbase(i)
1100          continue
c
1000    continue
            write (*,*)
130         format(10x,20(1x,i1),5x,i5)
            write(*,*)
            write(*,120) jj
120         format(1x,'Number of words=',i5)
c
c
            end
```

APPENDIX 1c
Exemplary computer program for generating
minimally cross hybridization sets
(double stranded tag/single stranded tag complement)

```
Program 3tagN
c
c
c         Program 3tagN generates minimally cross-hybridizing
c            sets of duplex subunits given i) N--subunit length,
c            and ii) and initial homopurine sequence.
c
c
            character*1 sub1 (20)
            integer*2 mset(10000,20), nbase(20)
c
c
            write(*,*) 'ENTER SUBUNIT LENGTH'
            read(*,100)nsub
100         format(i2)
c
c
            write(*,*) 'ENTER SUBUNIT SEQUENCE a & g only'
            read(*,110) (sub(k),k=1,nsub)
110         format(20a1)
c
            ndiff=10
c
c           Let a=1 and g=2
c
            do 800 kk=1,nsub
              if(sub1(kk).eq.'a') then
                mset(1, kk)=1
              endif
              if(sub1(kk).eq.'g') then
                mset(1, kk)=2
              endif
800         continue
c
            jj=1
c
            do 1000 k1=1,3
              do 1000 k2=1,3
                do 1000 k3=1,3
                  do 1000 k4=1,3
                    do 1000 k5=1,3
                      do 1000 k6=1,3
                        do 1000 k7=1,3
                          do 1000 k8=1,3
                            do 1000 k9=1,3
                              do 1000 k10=1,3
          do 1000 k11=1,3
            do 1000 k12=1,3
              do 1000 k13=1,3
                do 1000 k14=1,3
                  do 1000 k15=1,3
                    do 1000 k16=1,3
                      do 1000 k17=1,3
                        do 1000 k18=1,3
                          do 1000 k19=1,3
```

-continued

APPENDIX 1c
Exemplary computer program for generating
minimally cross hybridization sets
(double stranded tag/single stranded tag complement)

```
              do 1000 k20=1,3
                  nbase (1)=k1
                  nbase (2)=k2
                  nbase (3)=k3
                  nbase (4)=k4
                  nbase (5)=k5
                  nbase (6)=k6
                  nbase (7)=k7
                  nbase (8)=k8
                  nbase (9)=k9
                  nbase (10)=k10
                  nbase (11)=k11
                  nbase (12)=k12
                  nbase (13)=k13
                  nbase (14)=k14
                  nbase (15)=k15
                  nbase (16)=k16
                  nbase (17)=k17
                  nbase (18)=k18
                  nbase (19)=k19
                  nbase (20)=k20
c
              do 1250 nn=1,jj
c
                  n=0
                  do 1200 j=1,nsub
                      if(mset(nn,j).eq.1 .and. nbase(j).ne.1 .or.
                          mset(nn,j).eq.2 .and. nbase(j).ne.2 .or.
                          mset(nn,j).eq.3 .and. nbase(j).ne.3 .or.
                          mset(nn,j).eq.4 .and. nnase(j).ne.4) then
                          n=n+1
                      endif
```

-continued

APPENDIX 1c
Exemplary computer program for generating
minimally cross hybridization sets
(double stranded tag/single stranded tag complement)

```
1200              continue
c
                  if(n.lt.ndiff) then
                      goto 1000
                  endif
1250          continue
c
                  jj=jj+1
                  write(*,130)(nbase(i),i=1,nsub),jj
                  do 1100 i=1,nsub
                      mset(jj,i)=nbase(i)
1100              continue
c
1000          continue
c
                  write(*,*)
130               format(10x,20(1x,i1),5x,i5)
                  write(*,*)
                  write(*,120) jj
120               format(1x, 'Number of words=',i5)
c
c
                  end
```

I claim:

1. A method of determining the toxicity of a compound, the method comprising the steps of:
   administering the compound to a test organism;
   extracting a population of mRNA molecules from each of one or more tissues of the test organism;
   forming a separate population of cDNA molecule from each population of mRNA molecules from the one or more tissues such that each cDNA molecule of the separate populations has an oligonucleotide tag attached, the oligonucleotide tags being selected from the same minimally cross-hybridizing set;
   separately sampling each separate population of cDNA molecules such that substantially all different cDNA molecules within a sample have different oligonucleotide tags attached;
   sorting the cDNA molecules of each sample by specifically hybridizing the oligonucleotide tags with their respective complements, the respective complements being attached as uniform populations of substantially identical complements in spatially discrete regions on one or more solid phase supports;
   determining the nucleotide sequence of a portion of each of the sorted cDNA molecules of each separate population to form a frequency distribution of expressed genes for each of the one or more tissues; and
   determining the toxicity of the compound from the frequency distribution of expressed genes in each of the one or more tissues.

2. The method of claim 1 wherein said oligonucleotide tag and said complement of said oligonucleotide tag are single stranded.

3. The method of claim 2 wherein said oligonucleotide tag consists of a plurality of subunits, each subunit consisting of an oligonucleotide of 3 to 9 nucleotides in length and each subunit being selected from the same minimally cross-hybridizing set.

4. The method of claim 3 wherein said one or more solid phase supports are microparticles and wherein said step of sorting said cDNA molecules onto the microparticles produces a subpopulation of loaded microparticles and a subpopulation of unloaded microparticles.

5. The method of claim 4 further including a step of separating said loaded microparticles from said unloaded microparticles.

6. The method of claim 5 further including a step of repeating said steps of sampling, sorting, and separating until the number of said loaded microparticles that is accumulated is at least 10,000.

7. The method of claim 6 wherein said number of loaded microparticles is at least 100,000.

8. The method of claim 7 wherein said number of loaded microparticles is at least 500,000.

9. The method of claim 5 further including a step of repeating said steps of sampling, sorting, and separating until the number of said loaded microparticles that is accumulated is sufficient to estimate the relative abundance of a cDNA molecule present in said population at a frequency within the range of from 0.1% to 5% with a 95% confidence limit no larger than 0.1% of said population.

10. The method of claim 4 wherein said test organism is a mammalian tissue culture.

11. The method of claim 10 wherein said mammalian tissue culture comprises hepatocytes.

12. The method of claim 4 wherein said test organism is an animal selected from the group consisting of rats, mice, hamsters, guinea pigs, rabbits, cats, dogs, pigs, and monkeys.

13. The method of claim 12 wherein said one or more tissues are selected from the group consisting of liver, kidney, brain, cardiovascular, thyroid, spleen, adrenal, large intestine, small intestine, pancreas, urinary bladder, stomach, ovary, testes, and mesenteric lymph nodes.

14. A method of identifying genes which are differentially expressed in a selected tissue of a test animal after treatment with a compound, the method comprising the steps of:

administering the compound to a test animal;

extracting a population of mRNA molecules from the selected tissue of the test animal;

forming a population of cDNA molecules from the population of mRNA molecules such that each cDNA molecule has an oligonucleotide tag attached, the oligonucleotide tags being selected from the same minimally cross-hybridizing set;

sampling the population of cDNA molecules such that substantially all different cDNA molecules have different oligonucleotide tags attached;

sorting the cDNA molecules by specifically hybridizing the oligonucleotide tags with their respective complements, the respective complements being attached as uniform populations of substantially identical complements in spatially discrete regions on one or more solid phase supports;

determining the nucleotide sequence of a portion of each of the sorted cDNA molecules to form a frequency distribution of expressed genes; and identifying genes expressed in response to administering the compound by comparing the frequencing distribution of expressed genes of the selected tissue of the test animal with a frequency distribution of expressed genes of the selected tissue of a control animal.

15. The method of claim 14 wherein said oligonucleotide tag and said complement of said oligonucleotide tag are single stranded.

16. The method of claim 15 wherein said oligonucleotide tag consists of a plurality of subunits, each subunit consisting of an oligonucleotide of 3 to 9 nucleotides in length and each subunit being selected from the same minimally cross-hybridizing set.

17. The method of claim 16 wherein said one or more solid phase supports are microparticles and wherein said step of sorting said cDNA molecules onto the microparticles produces a subpopulation of loaded microparticles and a subpopulation of unloaded microparticles.

18. The method of claim 17 further including a step of separating said loaded microparticles from said unloaded microparticles.

19. The method of claim 18 further including a step of repeating said steps of sampling, sorting, and separating until the number of said loaded microparticles that is accumulated is at least 10,000.

20. The method of claim 19 wherein said number of loaded microparticles is at least 100,000.

* * * * *